(12) United States Patent
Soreq et al.

(10) Patent No.: US 10,174,320 B2
(45) Date of Patent: Jan. 8, 2019

(54) DOWNREGULATING MIR-132 FOR THE TREATMENT OF LIPID RELATED DISORDERS

(71) Applicant: Yissum Research Development Company of the Hebrew University of Jerusalem Ltd., Jerusalem (IL)

(72) Inventors: Hermona Soreq, Jerusalem (IL); Geula Hanin, Jerusalem (IL); David S. Greenberg, Jerusalem (IL)

(73) Assignee: Yissum Research Development Company of the Hebrew University of Jerusalem Ltd., Jerusalem (IL)

(*) Notice: Subject to any disclaimer, the term of this patent is extended or adjusted under 35 U.S.C. 154(b) by 0 days.

(21) Appl. No.: 15/511,648

(22) PCT Filed: Sep. 21, 2015

(86) PCT No.: PCT/IL2015/050956
§ 371 (c)(1),
(2) Date: Mar. 16, 2017

(87) PCT Pub. No.: WO2016/042561
PCT Pub. Date: Mar. 24, 2016

(65) Prior Publication Data
US 2017/0283800 A1    Oct. 5, 2017

Related U.S. Application Data

(60) Provisional application No. 62/135,206, filed on Mar. 19, 2015, provisional application No. 62/079,009, filed on Nov. 13, 2014, provisional application No. 62/053,167, filed on Sep. 21, 2014.

(51) Int. Cl.
| | | |
|---|---|---|
| *A61K 48/00* | (2006.01) |
| *C07H 21/02* | (2006.01) |
| *C07H 21/04* | (2006.01) |
| *C12N 15/113* | (2010.01) |

(52) U.S. Cl.
CPC ...... *C12N 15/113* (2013.01); *C12N 2310/113* (2013.01); *C12N 2310/315* (2013.01); *C12N 2310/321* (2013.01); *C12N 2310/3231* (2013.01); *C12N 2320/31* (2013.01); *C12N 2320/35* (2013.01)

(58) Field of Classification Search
CPC .. C12N 15/113; C12N 2310/11; A61K 31/713
See application file for complete search history.

(56) References Cited

U.S. PATENT DOCUMENTS

2012/0178791 A1    7/2012  Kowalik et al.
2017/0002428 A1*   1/2017  Kerin et al. ......... C12N 15/113

FOREIGN PATENT DOCUMENTS

| WO | WO 2007/027894 | 3/2007 |
| WO | WO 2007/112754 | 10/2007 |
| WO | WO 2010/105096 | 9/2010 |
| WO | WO 2013/034653 | 3/2013 |
| WO | WO 2016/042561 | 3/2016 |

OTHER PUBLICATIONS

Wahlestedt et al., PNAs, 2000, vol. 97, No. 10, 5633-5638.*
Communication Relating to the Results of the Partial International Search dated Jan. 25, 2016 From the International Searching Authority Re. Application No. PCT/IL2015/050956.
International Preliminary Report on Patentability dated Mar. 30, 2017 From the International Bureau of WIPO Re. Application No. PCT/IL2015/050956. (11 Pages).
International Search Report and the Written Opinion dated Apr. 6, 2016 From the International Searching Authority Re. Application No. PCT/IL2015/050956.
Bala et al. "MicroRNA Signature in Alcoholic Liver Disease", International Journal of Hepatology, XP002752841, 2012: 1-6, 2012.
Estep et al. "Differential Expression of MiRNAs in the Visceral Adipose Tissue of Patients With Non-Alcoholic Fatty Liver Disease", Alimentary Pharmacology & Therapeutics, XP055019336, 32(3): 487-497, Aug. 1, 2010.
Heneghan et al. "Role of MicroRNAs in Obesity and the Metabolic Syndrome", Obesity Reviews, XP002634305, 11(5): 354-361, May 1, 2010.
Mulik et al. "Potential Function of MiRNAs in Herpetic Stromal Keratitis", Investigative Ophthalmology & Visual Science, 54(1): 563-573, Jan. 2013.
Wei "Roles of MicroRNAs in Fatty Liver Lipid Accumulation", A Thesis Submitted for the Degree of Master of Science, Department of Biochemistry, National University of Singapore, 117 P., 2012.
Westenskow et al. "Using Flow Cytometry to Compare the Dynamics of Photoreceptor Outer Segment Phagocytosis in iPS-Derived RPE Cells", Investigative Ophthalmology & Visual Science, 53(10): 6282-6290, Sep. 2012.
Zhang et al. "MiR-132 Inhibits Expression of SIRT1 and Induces Pro-Inflammatory Processes of Vascular Endothelial Inflammation Through Blockade of the SREBP-1c Metabolic Pathway", Cardiovascular Drugs and Therapy, XP055239841, 28(4): 303-311, Published Online Jun. 13, 2014.
Communication Pursuant to Article 94(3) EPC dated Jun. 6, 2018 From the European Patent Office Re. Application No. 15785195.7. (5 Pages).

* cited by examiner

Primary Examiner — Amy H. Bowman

(57) ABSTRACT

A method of treating a lipid-related disorder in a subject in need thereof is disclosed. The method comprises administering to the subject a therapeutically effective amount of a polynucleotide agent which is substantially complementary to a nucleotide sequence of human miR-132, thereby treating the lipid related disorder in the subject.

19 Claims, 26 Drawing Sheets
(23 of 26 Drawing Sheet(s) Filed in Color)
Specification includes a Sequence Listing.

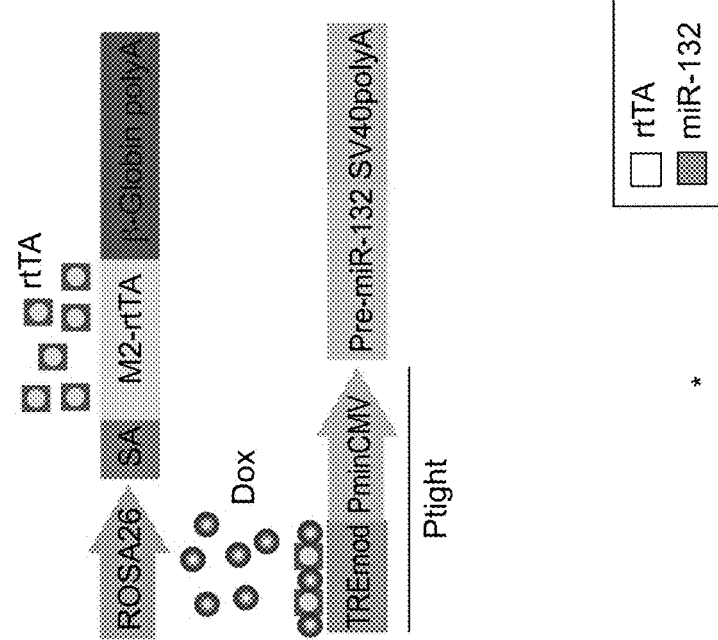
FIG. 1A
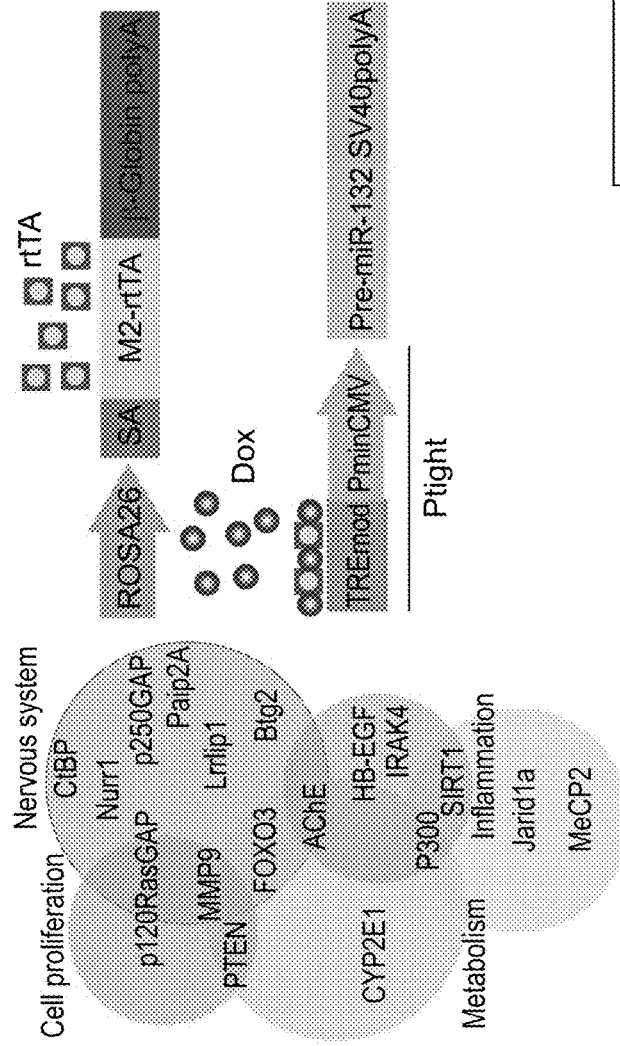
FIG. 1B
FIG. 1C

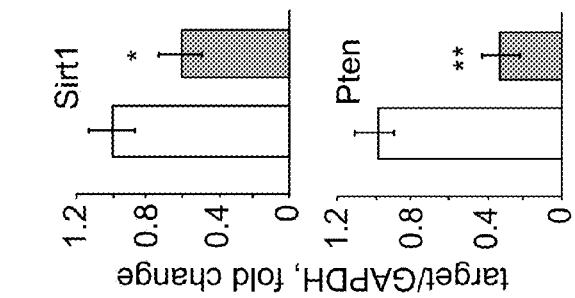
FIG. 1E
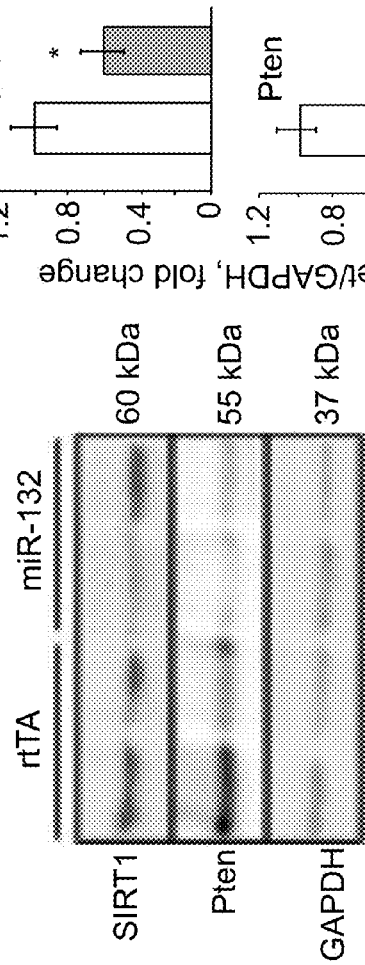
FIG. 1D
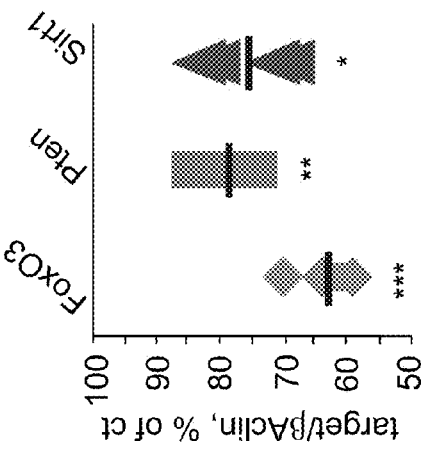
FIG. 1F
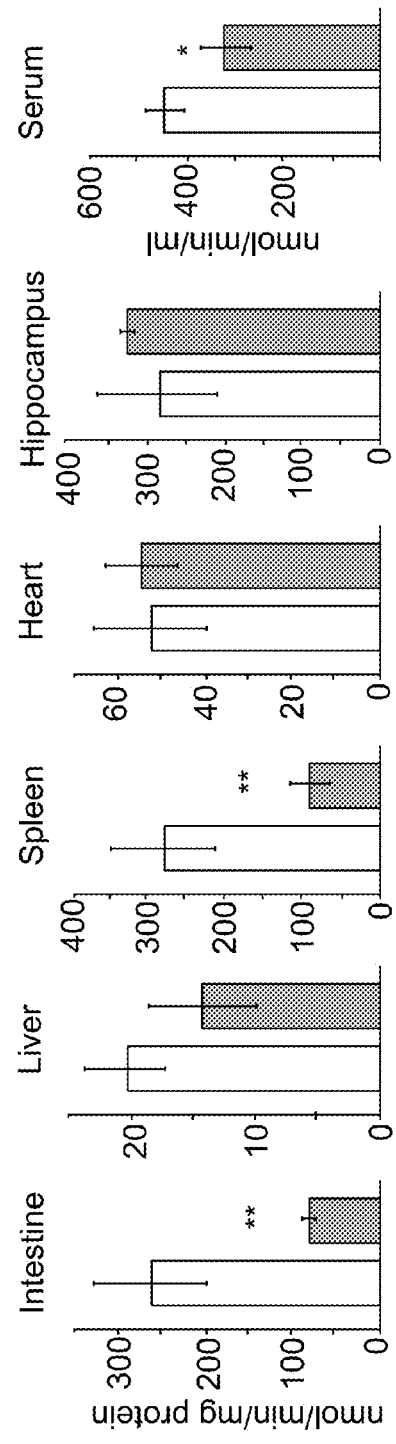

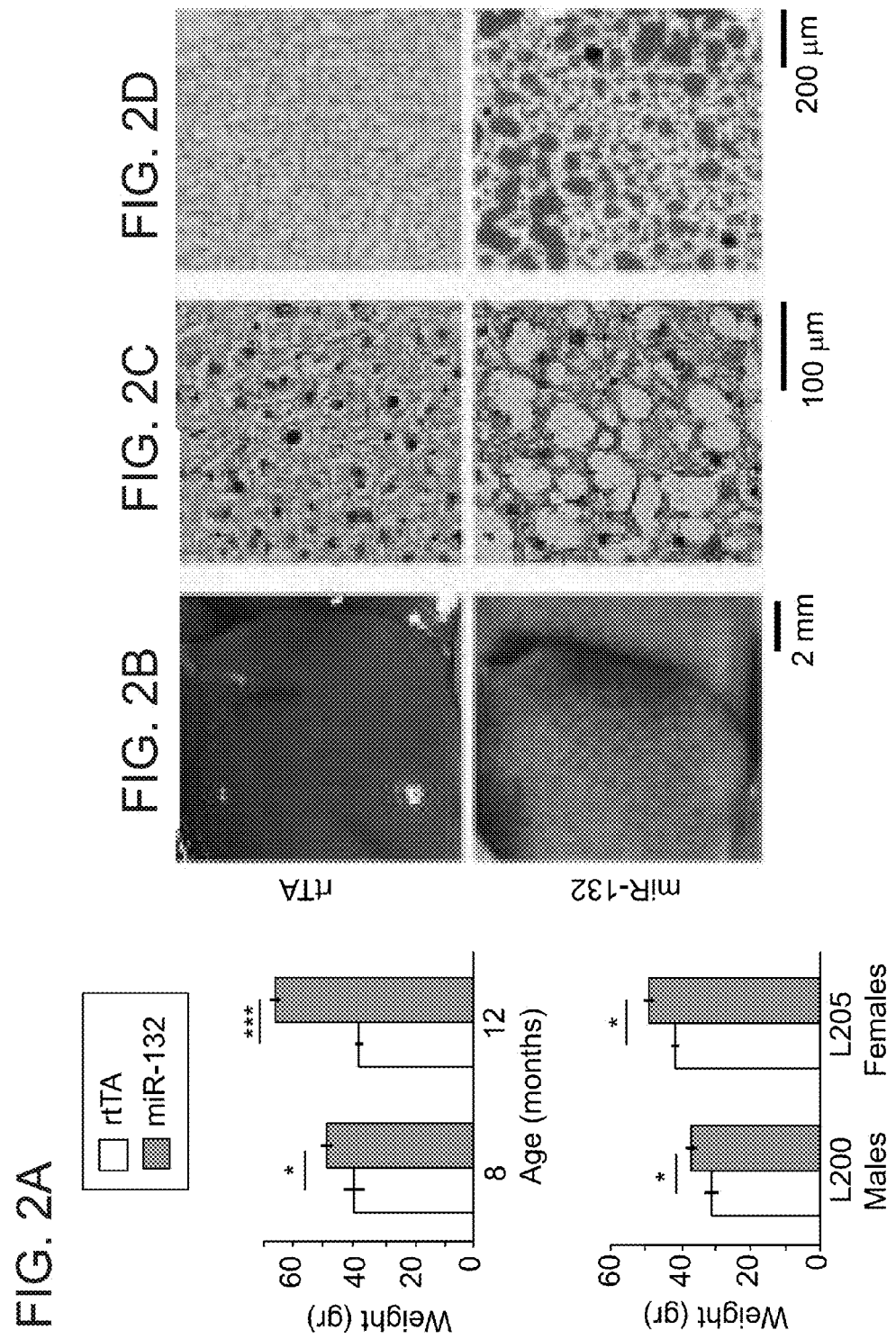

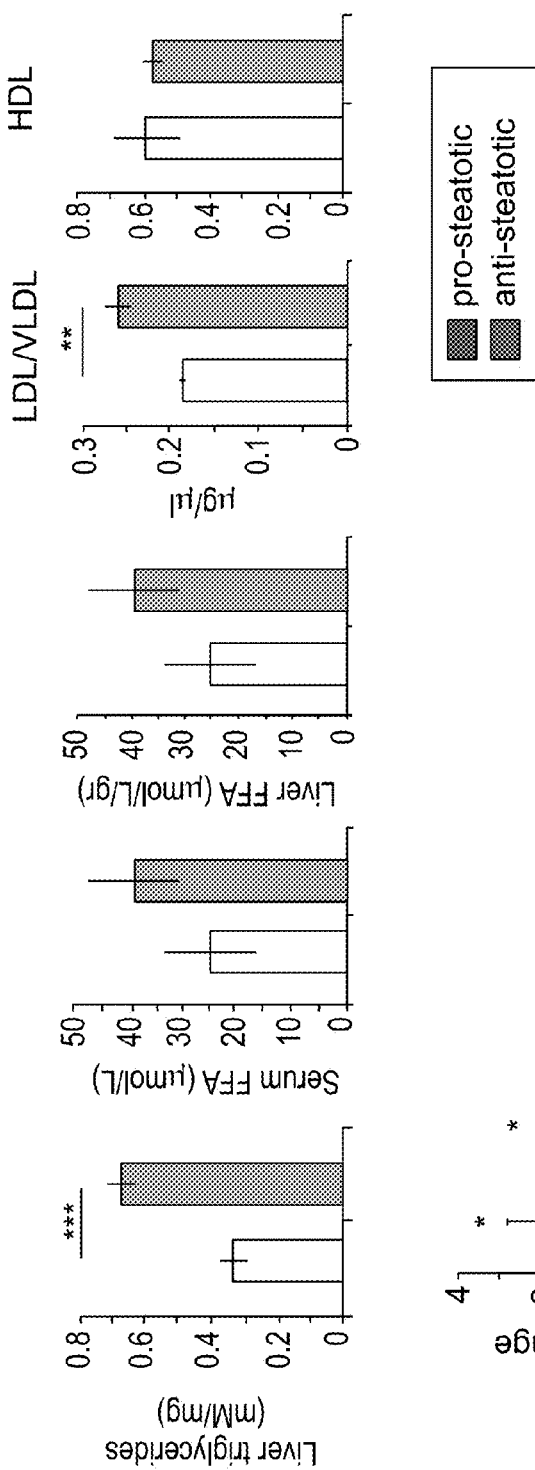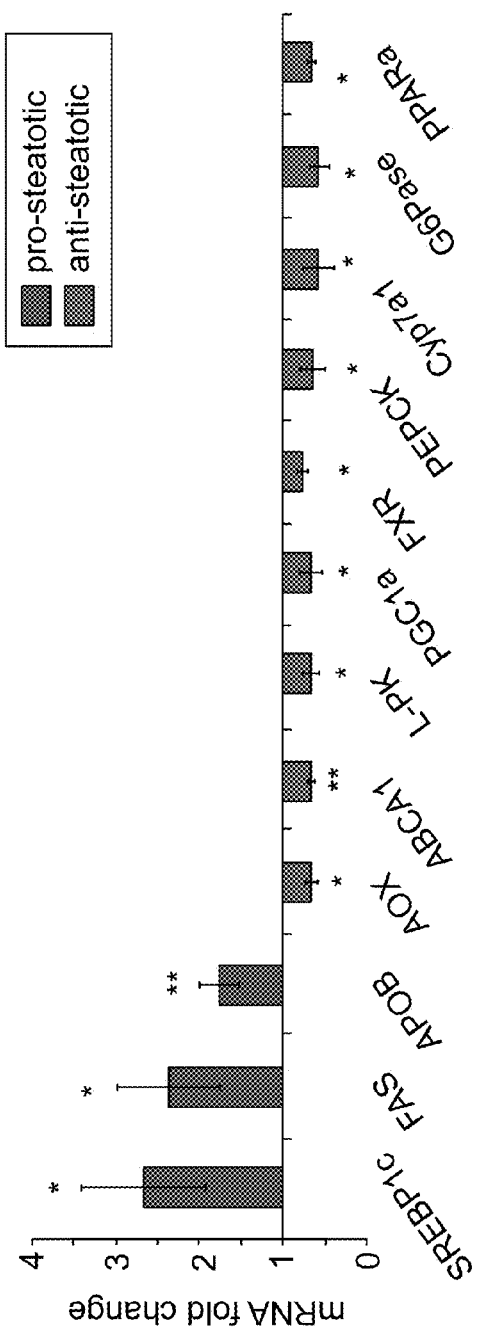

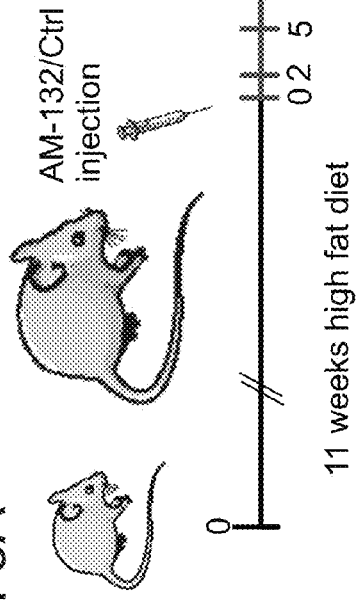
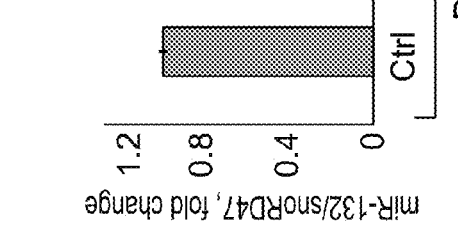
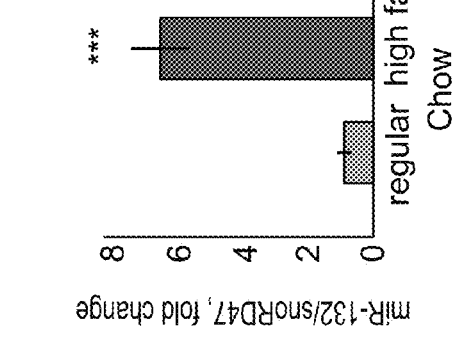
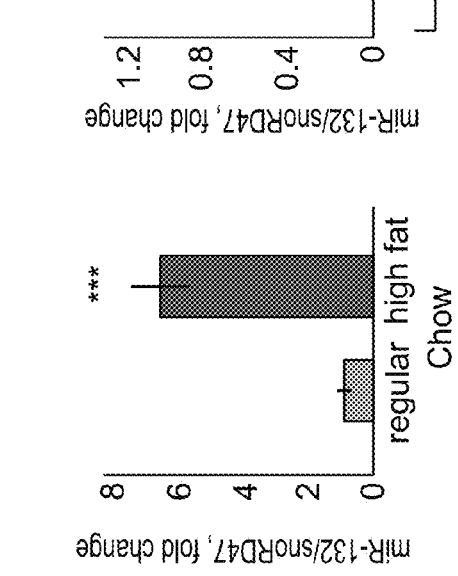
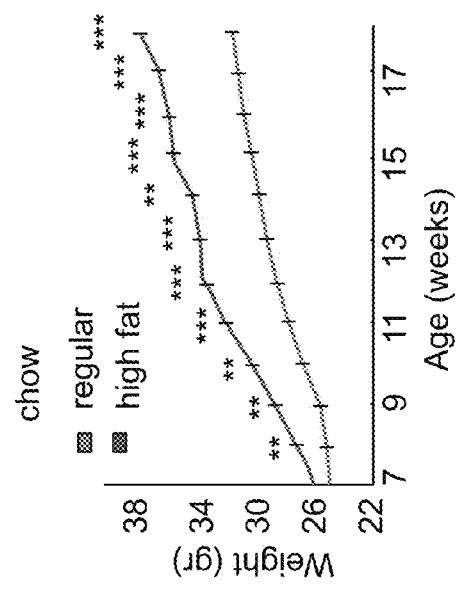
FIG. 3A
FIG. 3B
FIG. 3C
FIG. 3D

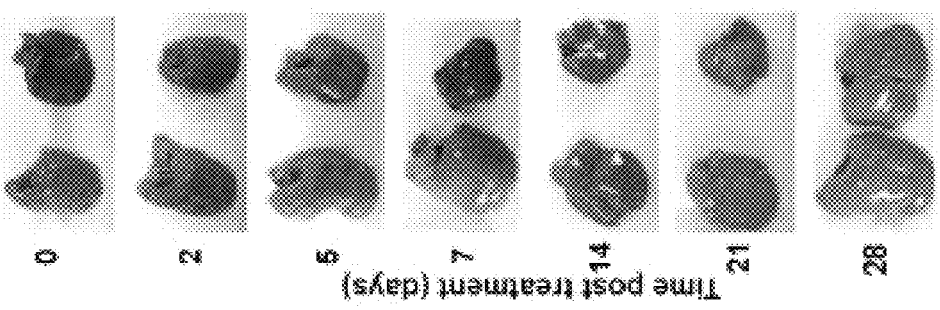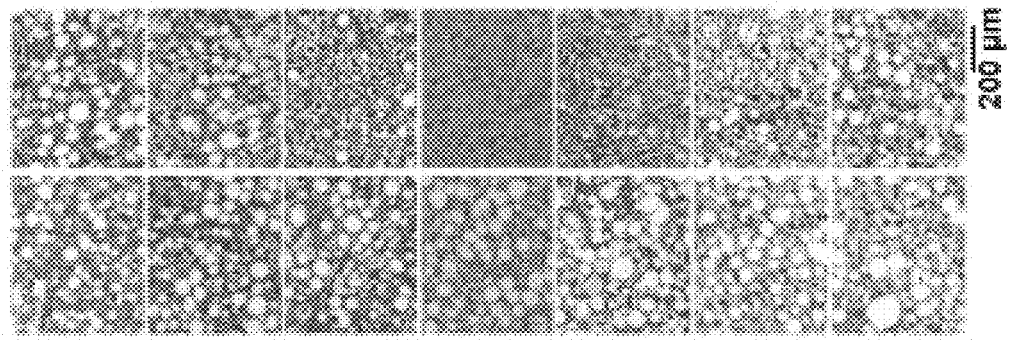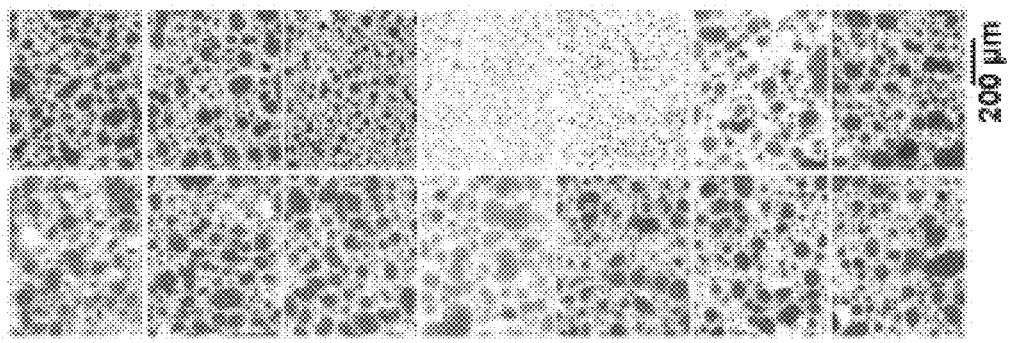

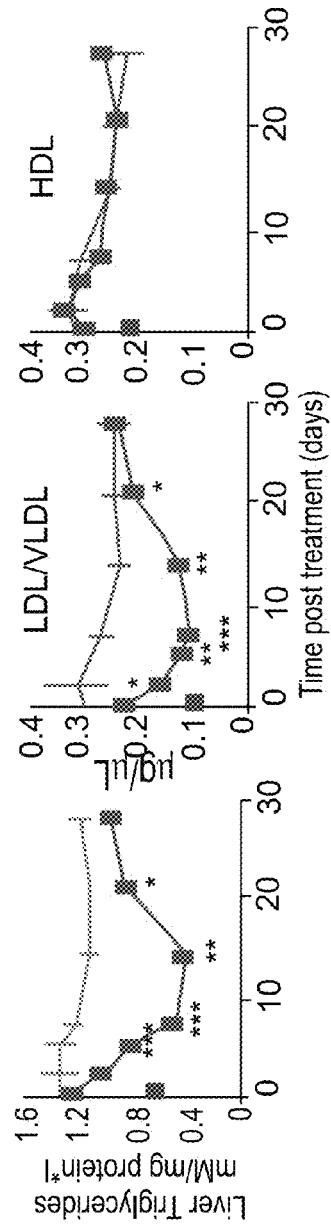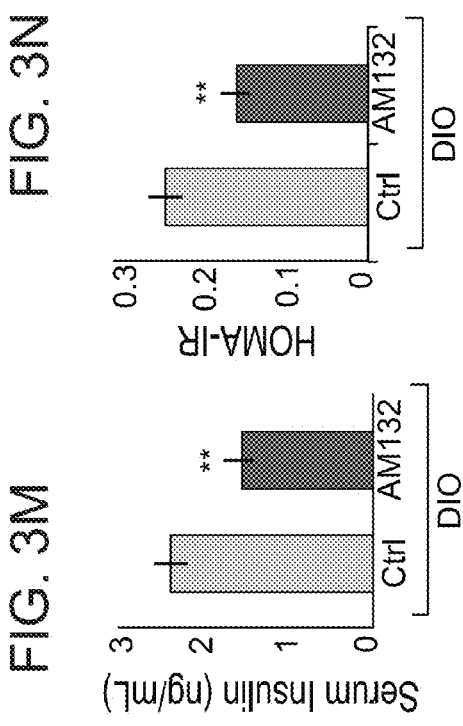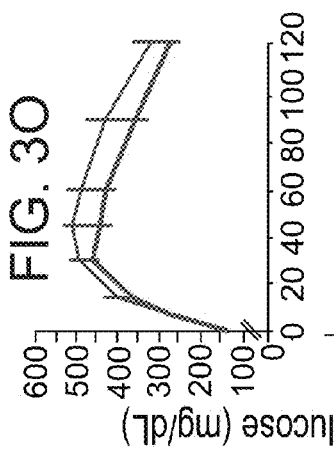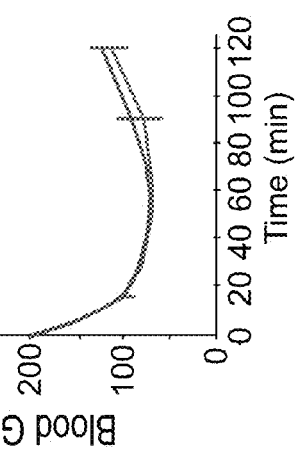

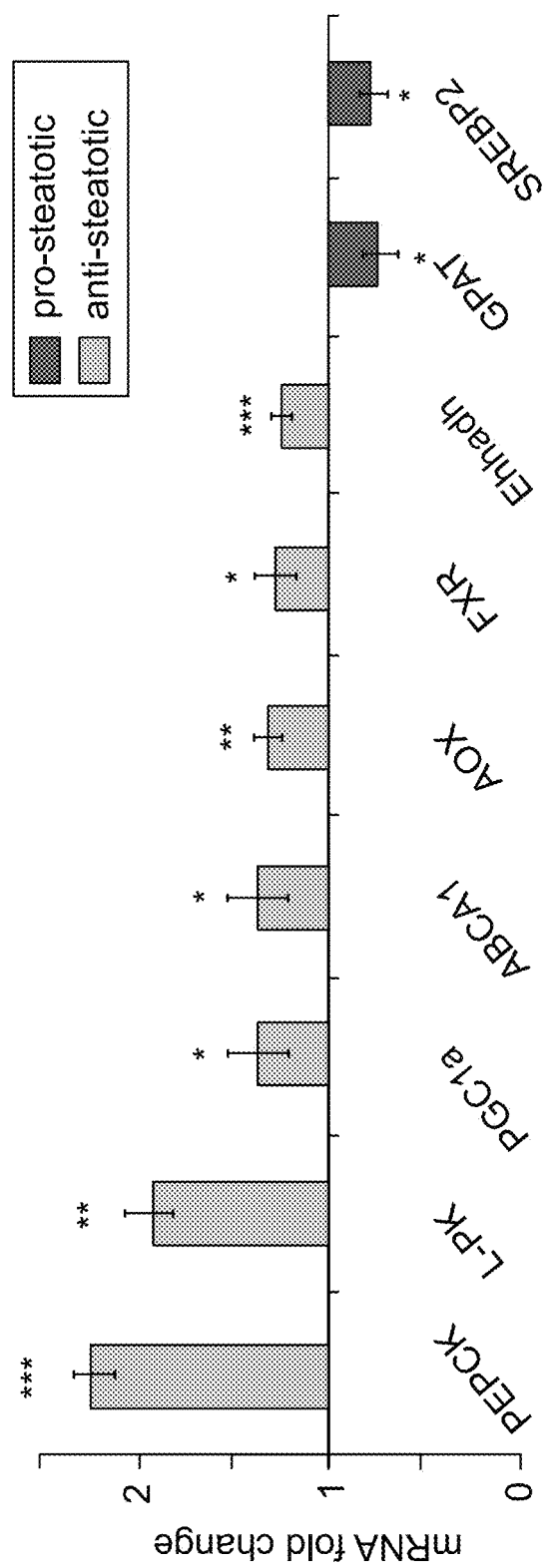

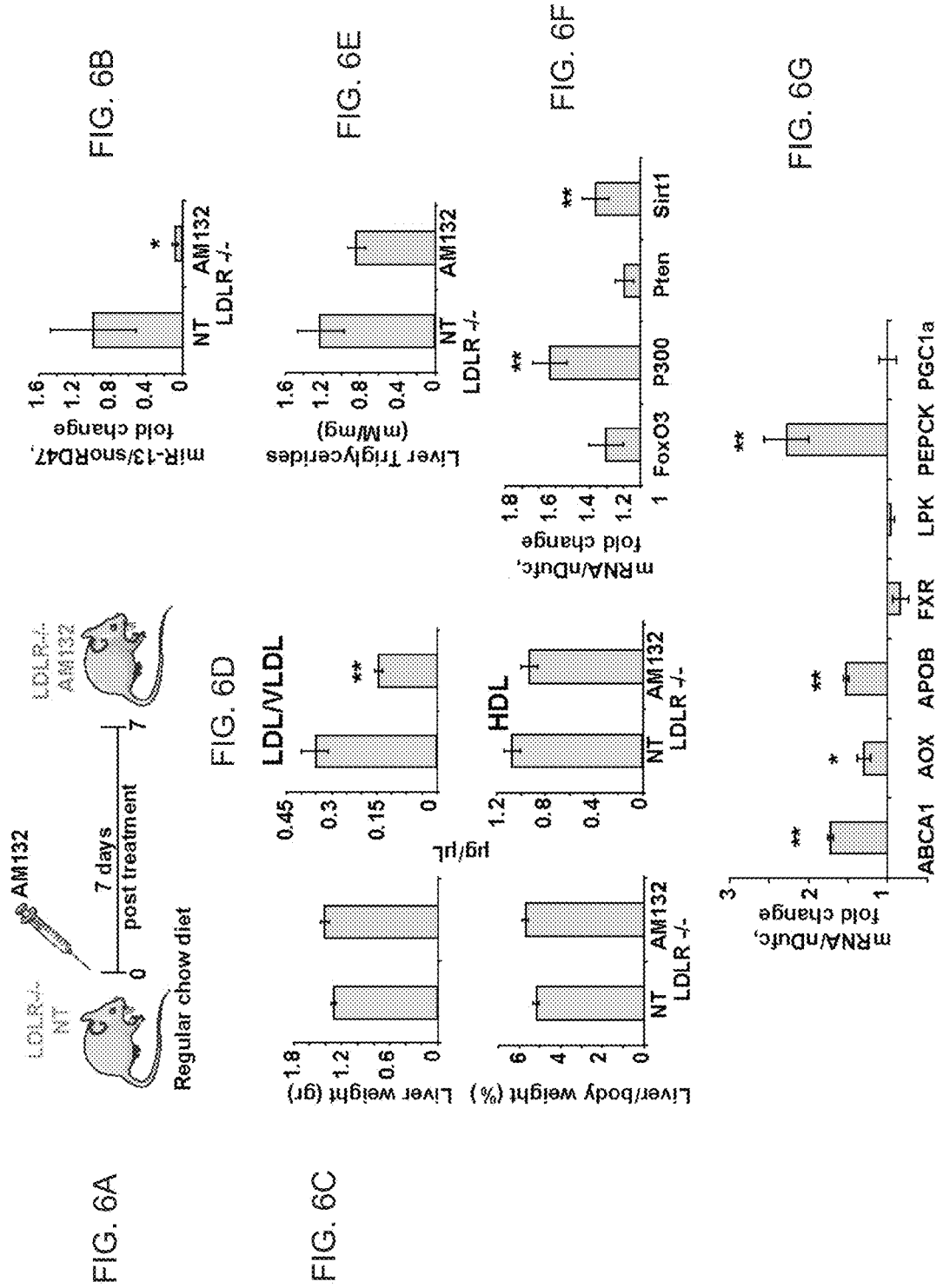

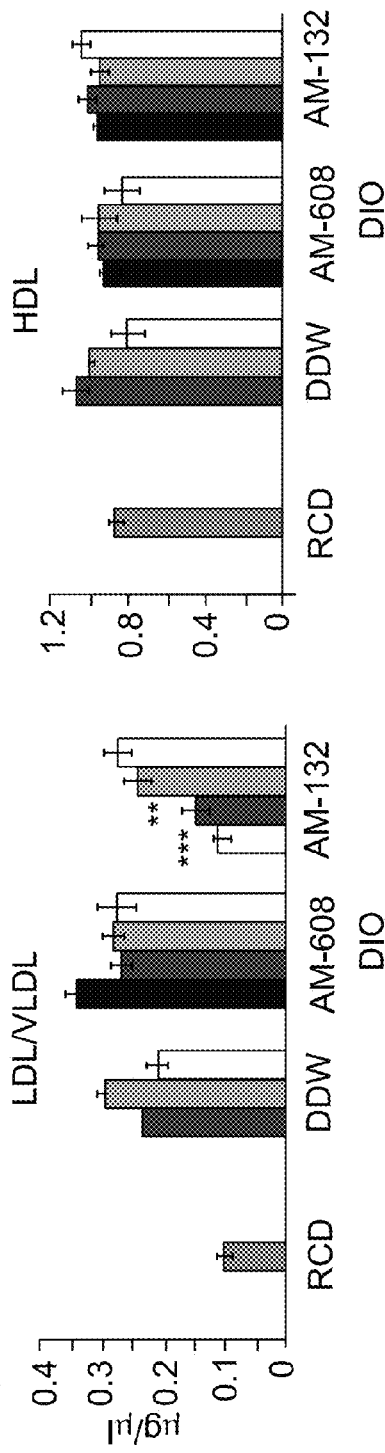
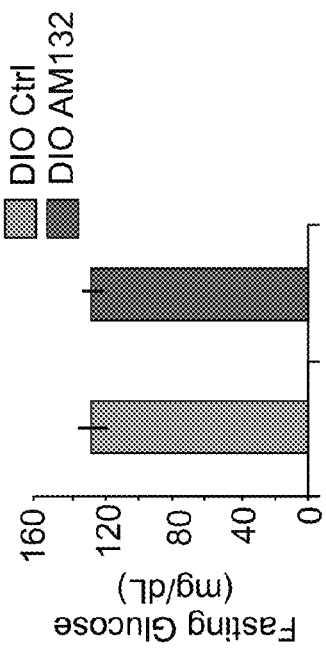
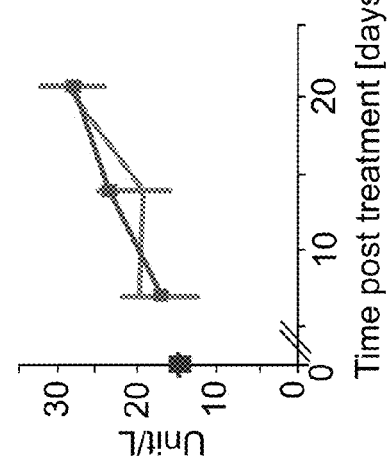
FIG. 8C
FIG. 8D
FIG. 8E

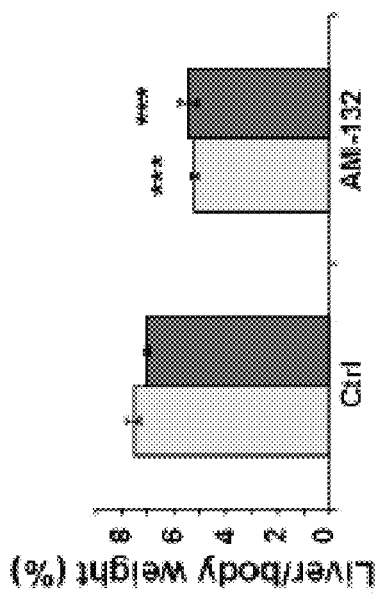
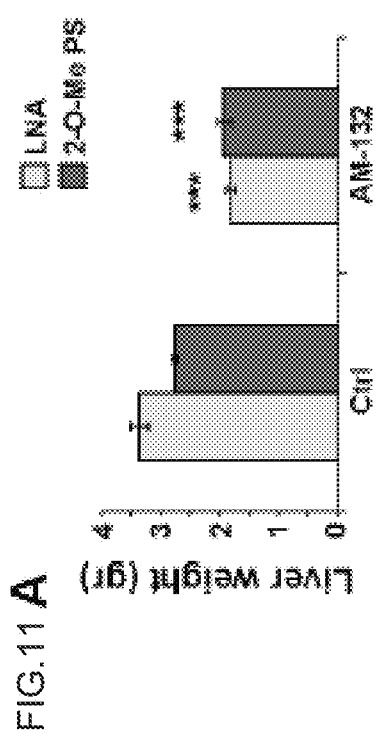
FIG. 11 A
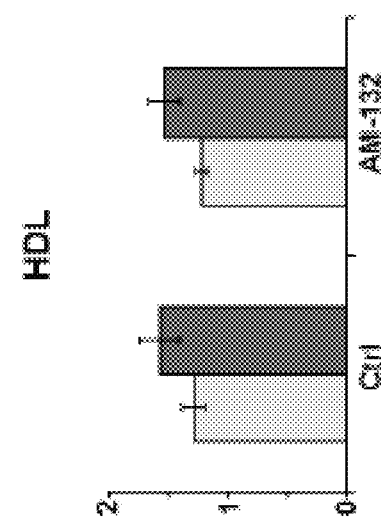
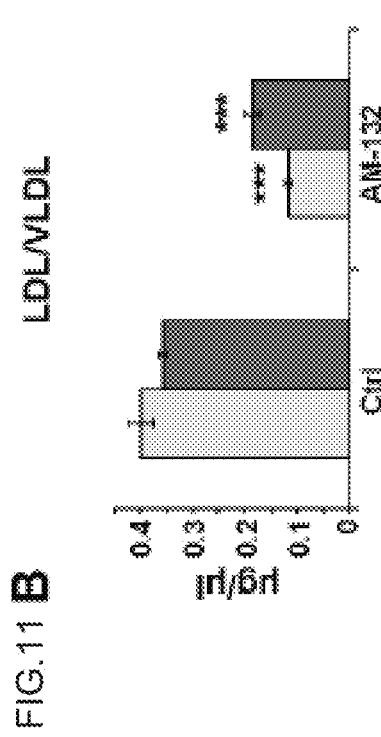
FIG. 11 B

DOWNREGULATING MIR-132 FOR THE TREATMENT OF LIPID RELATED DISORDERS

RELATED APPLICATIONS

This application is a National Phase of PCT Patent Application No. PCT/IL2015/050956 having International filing date of Sep. 21, 2015, which claims the benefit of priority under 35 USC § 119(e) of U.S. Provisional Patent Application Nos. 62/135,206 filed on Mar. 19, 2015, 62/079,009 filed on Nov. 13, 2014 and 62/053,167 filed on Sep. 21, 2014. The contents of the above applications are all incorporated by reference as if fully set forth herein in their entirety.

SEQUENCE LISTING STATEMENT

The ASCII file, entitled 69052SequenceListing.txt, created on Mar. 16, 2017, comprising 3,287 bytes, submitted concurrently with the filing of this application is incorporated herein by reference.

FIELD AND BACKGROUND OF THE INVENTION

The present invention, in some embodiments thereof, relates to a method of treating lipid-related disorders and, more particularly, but not exclusively, to fatty liver disorders.

Non-Alcoholic Fatty Liver Disease (NAFLD) affects 30% of adults in the US and is a key predisposing factor for nonalcoholic steatohepatitis (NASH), cirrhosis and hepatocellular carcinoma. NAFLD is accompanied by hyperlipidemia and is strongly associated with insulin resistance, obesity and type 2 diabetes. However, the mechanisms initiating this pathogenesis are not fully understood, and the available therapeutic interventions are of limited efficacy. NAFLD is characterized by accumulation of triglyceride lipid droplets in the cytoplasm of liver hepatocytes, yet the processes promoting this accumulation are still not understood.

In both the liver and the brain, control of metabolism is governed by a complex transcriptional system, in which microRNAs (miRNAs) function as critical regulators. MiRNA precursors (stem-and-loop molecules generated from a primary transcript) are cleaved to 22-bp mature double-stranded forms, one of which guides the complex to a partially complementary sequence often found in the 3'-untranslated region (3'-UTR) of target genes. The miRNA 5'-end 'seed' region determines target specificity and decides between mRNA cleavage and translational repression. Promiscuous complementation enables one miRNA to target more than one mRNA and achieve gene-network-level regulation. In the mammalian immune system, miRNAs control both differentiation and innate and adaptive immune responses. Each miRNA may target several mRNAs, often in specific locations on their 3'-UTR and can modulate entire pathways in a rheostat-like manner. MiRNAs act rapidly and effectively to block expression of their multiple target transcripts and operate at the network level, suggesting that they are particularly suitable for hierarchically controlling the rapidly adjustable physiology of entire physiological systems. Moreover, due to the multileveled regulation of a physiological system, very low concentrations of specific miRNAs could modulate multiple inputs such as both neuronal and immune pathways.

miR-132 has been identified as a hierarchically high regulator of such pathways (Soreq and Wolf, 2011, Trends Mol Med 17(10): 548-555; Shaltiel et al., 2013, Brain Struct Funct 218(1): 59-72; Greenberg and Soreq, 2014, Curr Pharm Des).

WO 2013034653 teaches administration of anti-miR-132 agents for the treatment of various diseases including liver disease.

Westenskow et al. (*Invest Ophthalmol Vis Sci* 2012; 53: E-Abstract 4120) teaches administration of anti-miR-132 agents for the treatment of eye disorders.

U.S. Patent Application No. 20120178791 teaches administration of anti-miR-132 agents for the treatment of HCMV.

SUMMARY OF THE INVENTION

According to an aspect of some embodiments of the present invention there is provided a method of treating a fatty liver disease in a subject in need thereof, comprising administering to the subject a therapeutically effective amount of a polynucleotide agent which is substantially complementary to a nucleotide sequence of human miR-132, thereby treating the fatty liver disease.

According to an aspect of some embodiments of the present invention there is provided a method of treating obesity in a subject in need thereof, comprising administering to the subject a therapeutically effective amount of a polynucleotide agent which is substantially complementary to a nucleotide sequence of human miR-132, thereby treating the obesity in the subject.

According to an aspect of some embodiments of the present invention there is provided an article of manufacture comprising a polynucleotide agent which is substantially complementary to a nucleotide sequence of human miR-132 and an-anti lipid agent.

According to an aspect of some embodiments of the present invention there is provided a polynucleotide agent which is substantially complementary to a nucleotide sequence of human miR-132, for treating obesity in a subject.

According to an aspect of some embodiments of the present invention there is provided a polynucleotide agent which is substantially complementary to a nucleotide sequence of human miR-132, for treating fatty liver disease in a subject.

According to an aspect of some embodiments of the present invention there is provided a method of treating a disease associated with weight loss in a subject in need thereof, the method comprising administering to a subject a therapeutically effective amount of human miR-132 or a mimic thereof, thereby treating the disease.

According to an aspect of some embodiments of the present invention there is provided a polynucleotide agent which is substantially complementary to a nucleotide sequence of human miR-132, for treating obesity in a subject.

According to an aspect of some embodiments of the present invention there is provided a polynucleotide agent which is substantially complementary to a nucleotide sequence of human miR-132, for treating fatty liver disease in a subject.

According to an aspect of some embodiments of the present invention there is provided a method of treating a disease associated with weight loss in a subject in need thereof, the method comprising administering to a subject a therapeutically effective amount of human miR-132 or a mimic thereof, thereby treating the disease.

According to some embodiments of the invention, the polynucleotide agent downregulates an amount of the human miR-132.

According to some embodiments of the invention, the polynucleotide agent downregulates an activity of the human miR-132.

According to some embodiments of the invention, the polynucleotide agent is double-stranded.

According to some embodiments of the invention, the polynucleotide agent is single-stranded.

According to some embodiments of the invention, the polynucleotide agent comprises the nucleic acid sequence as set forth in SEQ ID NO: 8 (5'-CGACCATGGCTGTA-GACTGTTA-3') or at least 15 consecutive bases thereof.

According to some embodiments of the invention, the polynucleotide agent comprises the nucleic acid sequence as set forth in SEQ ID NO: 7 (ATGGCTGTAGACTGTT) or SEQ ID NO: 10 (CGACCATGGCTGTAG).

According to some embodiments of the invention, the polynucleotide agent is at least 12 nucleotides in length.

According to some embodiments of the invention, the polynucleotide agent is at least 12-30 nucleotides in length.

According to some embodiments of the invention, the polynucleotide agent comprises a modified internucleotide linkage selected from the group consisting of phosphoroamidate, phosphorothiate, phosphorodithioate, boranophosphate, alkylphosphonate and methylinemethylimino.

According to some embodiments of the invention, the polynucleotide agent comprises a modified nucleic acid unit selected from the group consisting of locked nucleic acid unit, 2'-O-alkyl ribonucleic acid unit, 2'amine ribonucleic acid unit, peptide nucleic acid unit, 2'fluoro-ribo nucleic acid unit, morpholino nucleic acid unit, cyclohexane nucleic acid unit and a tricyclonucleic acid unit.

According to some embodiments of the invention, each of the nucleotides of said polynucleotide agent is a locked nucleic acid.

According to some embodiments of the invention, the nucleic acid unit comprises a modified nucleic acid unit selected from the group consisting of locked nucleic acid unit, 2'-O-methyl ribonucleic acid unit, and 2'O-methoxyethyl ribonucleic acid unit.

According to some embodiments of the invention, the polynucleotide agent comprises a locked nucleic acid, a 2'-O-methyl ribonucleic acid, or a mixed nucleic acid-locked nucleic acid.

According to some embodiments of the invention, the administering is effected once per day.

According to some embodiments of the invention, the administering is effected once a week.

According to some embodiments of the invention, the administering is effected once per two weeks.

According to some embodiments of the invention, the polynucleotide agent is administered systemically.

According to some embodiments of the invention, the dose of the polynucleotide agent is between 1 µg/kg body weight-100 mg/kg body weight per administration.

According to some embodiments of the invention, the dose of the polynucleotide agent is between 10 µg/kg body weight-100 mg/kg body weight per administration.

According to some embodiments of the invention, the dose of the polynucleotide agent is between 100 µg/kg body weight-100 mg/kg body weight per administration.

According to some embodiments of the invention, the dose of the polynucleotide agent is between 100 µg/kg body weight-10 mg/kg body weight per administration.

According to some embodiments of the invention, the dose of the polynucleotide agent is between 1 mg/kg body weight-10 mg/kg body weight per administration.

According to some embodiments of the invention, the subject does not have an eye disease.

According to some embodiments of the invention, the subject does not have a neurodegenerative disease.

According to some embodiments of the invention, the subject does not have cancer.

According to some embodiments of the invention, the fatty liver disease is selected from the group consisting of hypertriglyceridemia, steatohepatitis, atherosclerosis and hypercholesterolemia.

According to some embodiments of the invention, the hypercholesterolemia is a familial hypercholesterolemia.

According to some embodiments of the invention, the disease is selected from the group consisting of cancer, hyperthyroidism and anorexia.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 3H:
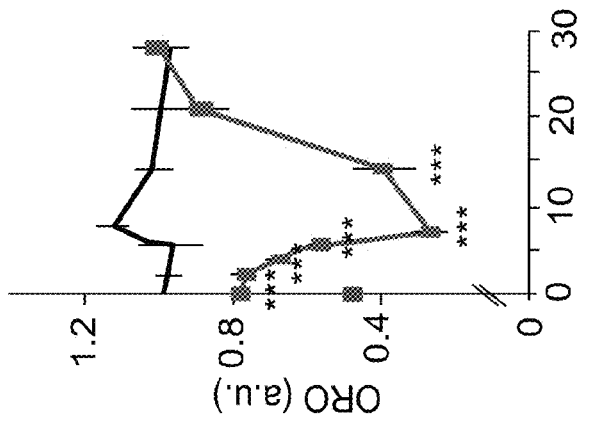
Figure 3I:
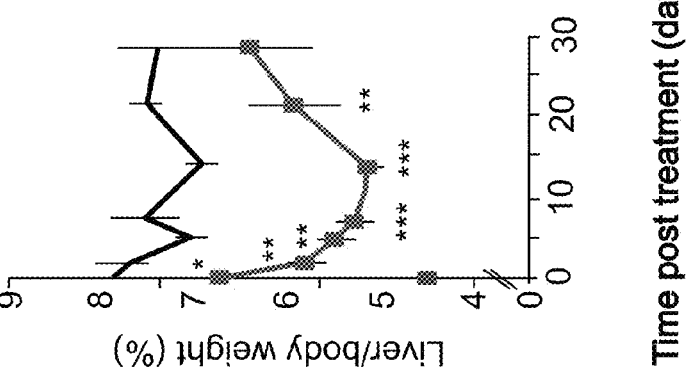
Figure 3J:
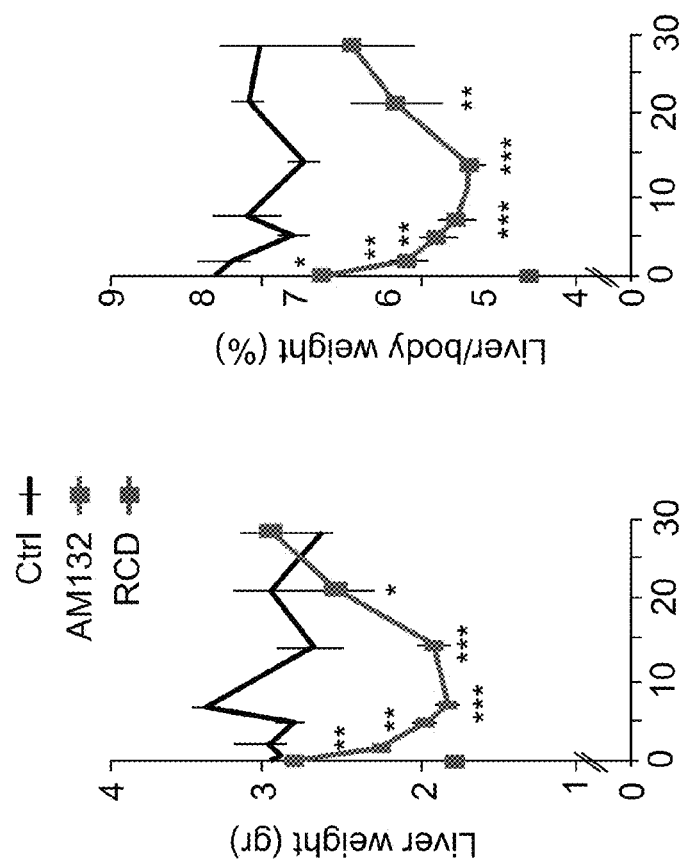

FIGS. 1A-F illustrate that peripheral miRNA-132 excess leads to multiple target reductions in diverse tissues. (A) Examples of reported MiRNA-132 targets and their biological functions. (B) Schematic representation of engineered doxycycline-inducible miRNA-132 vector: The reverse tetracycline controlled trans-activator (rtTA) followed by a β-globin poly A was inserted downstream of the Gt (ROSA) 26Sor promoter and the ColA1 locus. Pre-miRNA-132 under the Tet-responsive $P_{tight}$ promoter followed by an SV40 poly A was expressed in progeny of miR-132/dTg mated transgenic mice. The rtTA protein (orange squares) binds in trans to the $TRE_{mod}$ element in the presence of Doxycycline, allowing pre-miRNA-132 transcription. (C) Excess miRNA-132 levels in rtTA/miR-132dTg mice was observed in the heart, intestine, liver, spleen but not hippocampus (n=12 for rtTA, n=5 for miRNA-132). (D) Reduced mRNA levels of the miRNA-132 targets Sirt1, Pten and FoxO3 in liver from miRNA-132 tg mice. (n=3). (E) Protein blot and quantified reductions in Sirt1 and Pten in livers of miRNA-132 tg mice (n=6). (F) Suppressed AChE activity in miRNA-132 tg tissues (n=4). All data are representative of 3 experiments, *p<0.05, **p<0.01, and determined by Student's t-test, Values are expressed as mean+ standard evaluation of mean (s.e.m).

FIGS. 2A-H illustrate that miRNA-132 excess associates with liver steatosis and impaired lipid homeostasis. (A) miR-132 dTg mice gain more weight with age compared to their rtTA littermates; with (bottom) and without (top) Doxycycline induction, and in two independent transgenic lines (n=3). (B-G) Lipid accumulation in miR-132 dTg mice compared to rtTA littermates: (B) Representative image of fatty liver. (C, D) Liver sections stained by Hematoxylin/Eosin and Oil-Red O. (E) Increased liver Triglyceride storage at 8 months age (n=3). (F) Unchanged free fatty acid levels in liver and serum at 8 months (n=3). (G) Elevated LDL/VLDL but not HDL levels in serum (n=3). (H) Elevated pro-steatotic and reduced anti-steatotic transcripts in miR-132 dTg mice compared to rtTA obtained by Fluidigm analysis, normalized to multiple housekeeping genes and then to rtTA controls. (n=3). All data are representative of 2 experiments, *p<0.05, p<0.01, *p<0.001 and determined by Student's t-test. Bars show mean±s.e.m.

FIGS. 3A-O illustrate that MiRNA-132 suppression reduces liver weight, fat vacuoles, triglycerides, LDL/VLDL and insulin. (A) Experimental design: C57Bl/6J mice, high fat diet fed (DIO) for 11 weeks were injected with AM132 or control oligonucleotide for 3 days and sacrificed when noted. (B) Weights of DIO mice compared to regular chow diet (RCD). (n=20) (C, D) Endogenous liver miRNA-132 levels in DIO and RCD mice without (n=4) and 7 days post anti-miRNA-132 (AM132) treatment (n=4). (E) Representative DIO mice liver sections post-treatment. (F) Hematoxylin/Eosin stained liver sections. (G, K) Oil-red O staining micrographs and quantification results (n=3). (H-I) Reduced liver weight and liver/body weight of AM132-treated DIO mice. (n=4-9) (J) AM132 treatment leads to gradual transient reduction of liver triglycerides. (n=4-9) (L) LDL/VLDL but not HDL reduction in sera of AM132 treated mice (n=4-9). (M) Reduced fasting insulin levels in DIO-AM132 treated mice compared to controls. (n=8). (N) Top: Calculated sera HOMA-IR values in AM132 treated DIO mice (n=8). (O) Slightly improved glucose tolerance in AM132 treated DIO mice 7 days post treatment (n=8). Bottom: Unchanged insulin tolerance in AM132 treated mice compared to controls (n=8.). All data are representative of 3 experiments, *p<0.05, p<0.01, *p<0.001 AM132 compared to control and determined Student's t-test. Bar show mean±s.e.m. Staining included 10 fields/staining.

FIGS. 4A-D illustrate that miRNA-132 suppression upregulates its liver targets. (A) Elevated liver miRNA-132 target transcripts in AM132 treated DIO mice. Fluidigm reaction, normalized to multiple housekeeping genes and then to control treatment (n=4). (B) Protein blot and quantified elevation of liver Sirt1 and Pten in AM132-treated mice. (C) Immunofluorescence and quantified FoxO3 and P300 elevation in liver sections, Arginase 1 served as a hepatocyte marker (n=3-4). Quantification was performed in areas that did not contain fat vacuoles. (D) Increased pro-steatotic and reduced anti-steatotic metabolic transcripts in AM132 treated mice 7 days post treatment (n=4). All data are representative of 3 experiments, *p<0.05, p<0.01, *p<0.001 and determined by Student's t-test. All data are shown as mean±s.e.m.

FIGS. 5A-E illustrate that knockdown of FoxO3 and Pten in DIO mice mimics the hepatic impact of miRNA-132. (A) Experimental design: C57Bl/6J mice were DIO fed for 9 weeks, followed by a single intravenous injection of 10 mg/kg antisense GapmeR for FoxO3, Pten, P300, Sirt1 or negative control. Mice were sacrificed 7 days post treatment. (B) Elevated liver weight and liver/body weight in FoxO3 and Pten AS treated mice, and reduced liver weight and liver/body weight in P300 AS treated mice (n=4) (C) Hematoxylin/Eosin staining of liver sections. (D) Increased LDL/VLDL in FoxO3 and Pten antisense treated mice and unchanged HDL (n=4). (E) Target mRNA levels obtained from Fluidigm reaction, normalized to multiple housekeeping genes and then to Negative control-treated mice (n=4). *p<0.05, p<0.01, *p<0.001 and determined by two-way ANOVA. Bars show mean±s.e.m.

FIGS. 6A-G illustrate that AM132 selectively reduces LDL/VLDL levels in LDLR-/- mice. (A) Experimental design: RCD-fed lean LDLR-/- mice with elevated LDL/VLDL levels were treated by 3-successive daily intravenous injections of 3.3 mg/kg AM132 or not treated. All parameters were measured 7 days post treatment. (B) Reduced levels of liver miR-132 in LDLR-/- mice 7 days post AM132 treatment. (C) Unchanged liver and liver/body weight (n=3-4). (D) Reduced serum LDL/VLDL but not HDL in AM132 treated LDLR-/- mice (n=3-4). (E) Slightly reduced liver triglycerides in LDLR-/- mice treated with AM132 (n=3-4) (F) Expression of miR-132 targets and metabolic transcripts (G) in livers of AM132 treated LDLR-/- mice (n=3-4). *p<0.05, p<0.01, *p<0.001 determined Student's t-test. All data are mean±s.e.m.

FIGS. 7A-F. (A) Representative nested real-time PCR genotyping results of miR-132 dTg mice, compared to their rtTA littermate controls. (B) Ratio of transgenic mice progeny. (C) Excess miRNA-132 levels observed in the heart, intestine, liver, spleen but not hippocampus of miR-132-dTg mice (n=12 for rtTA, n=5 for miRNA-132. P<0.05 in all cases). (D) Predicted structures of the potential binding site sequences of miRNA-132 with the AChE, Pten, Sirt1, and FoxO3 transcripts. (E) Non-significantly changed mRNA levels of the miRNA-132 targets: AChE-S, IRAK4 and P300 in various tissues from miRNA-132 mice. (n=5 for rtTA, n=7 for miRNA-132, n.s. in all cases). (F) Representative image of fatty liver in two additional transgenic miR-132 dTg lines.

FIGS. 8A-E. (A) Reduced liver weight and liver/body weight of mice treated with AM132 but not AM608 which served as control (n=3-9). (B) Gradual and transient reduction in liver triglycerides of mice treated with AM132. (n=3-9,) (C-D) Reduced LDL/VLDL but not HDL levels in sera of mice treated with AM132 (n=3-9). (D) Unchanged Aspartate Aminotransferase (AST) activity in sera of DIO mice treated with AM132 or controls (n=3-4). (E) Unchanged fasting glucose levels in DIO mice treated with AM132 or controls (n=8). *p<0.05, p<0.01, *p<0.001 and determined by two-way ANOVA. Bars show mean±s.e.m.

FIGS. 9A-D. Lean RCD fed mice treated with AM132 showed sustained liver weight and liver to body weight values (A), AST activity (B), liver triglycerides (C), LDL/VLDL and HDL (D), n=5, one-way ANOVA n.s. in all cases).

FIGS. 10A-F. DIO mice were fed with high fat diet for 11 weeks, treated with 0.8, 1.6, 3.3, or 10 mg/kg AM132 or control, for 1 or 3 successive days and sacrificed 7 days post treatment. (A) Representative pictures of mouse livers. (B) Quantification of liver weight and liver/body weight of mice treated with decreased dosage of AM132 or control. (n=4-5). (C) H&E staining of liver sections. Metabolic biomarkers: Liver triglycerides (D, n=4), Serum LDL/VLDL (E) and HDL (F), n=4,) of mice treated with decreased dosage of AM132 or control. *p<0.05, p<0.01, *p<0.001 and determined by one-way ANOVA. Bars show mean±s.e.m.

FIGS. 11A-B illustrate that the AM132 effect is seen with different protection chemistries, suggesting sequence-dependence. Comparison between LNA-based oligonucleotide and 2-O-methyl and fully phosphorothioated backbone oligonucleotide shows insignificant differences between the effect of differently-protected oligonucleotides on liver weight and liver/body weight (A) or on LDL/VLDL and HDL (B) (n=5-6). ***p<0.001 determined by one-way ANOVA. Bars show mean±s.e.m.

FIGS. 12A-E show the results of testing the potential of specific GapmeRs to suppress distinct miRNA-132 targets in C2C12 cell culture experiments. (A-D) In vitro validation of knockdown efficiency of diverse miRNA-132 target transcripts in the C2C12 mouse myoblast cell line: Cells were transfected using HiPerfect (Qiagen), and RNA was extracted 48 h post transfection. Validation was performed by qRT-PCR quantification in cell-extracted RNA preparations using multiple primers located outside of the GapmeR area. Knockdown is shown for Sirt1(A), FoxO3 (B), Pten (C) and P300 (D). (E) Liver triglyceride levels of mice treated with target antisense GapmeRs, as described in FIGS. 6A-G.

Figure 13A:
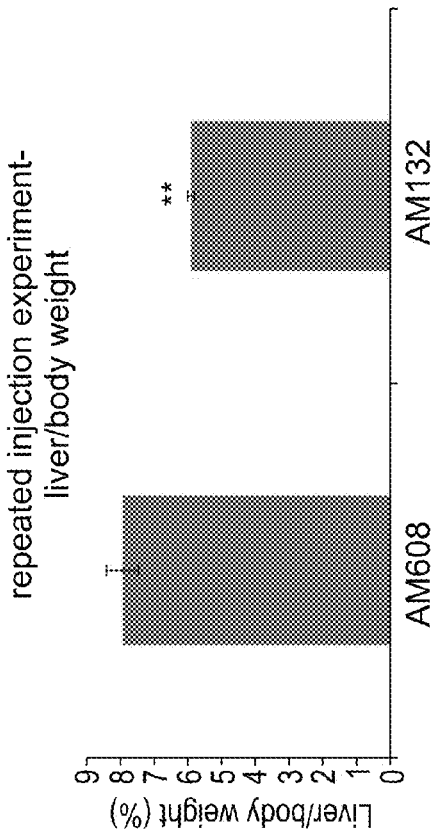
Figure 13B:
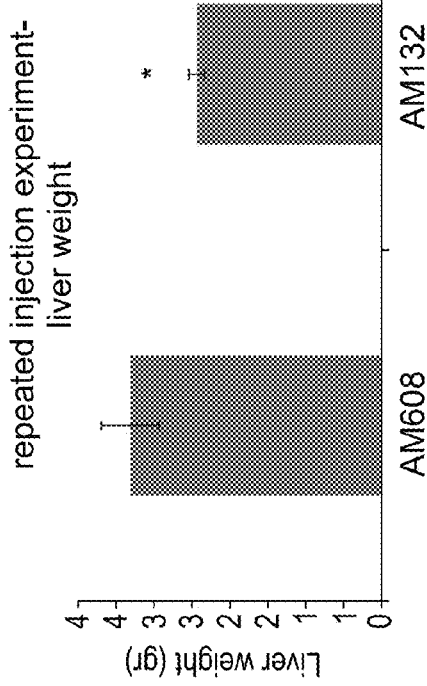

FIGS. 13A-B. Mice were fed with high fat diet for 11 weeks, treated with 10 mg/kg AM132 or control. 2 weeks later, these mice were injected again with the same oligonucleotide and dose. 11 days after the second injection mice were sacrificed. Liver weight (FIG. 13A) and liver/body weight (FIG. 13B) of AM132-treated mice were significantly reduced, similar to mice singly injected with of AM-132.

DESCRIPTION OF SPECIFIC EMBODIMENTS OF THE INVENTION

The present invention, in some embodiments thereof, relates to a method of treating lipid-related disorders and, more particularly, but not exclusively, to fatty liver diseases.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Non-Alcoholic Fatty Liver Disease (NAFLD) is a widespread condition with major health implications but incompletely understood mechanisms of induction. The present inventors have now shown that overexpression of microRNA (miRNA)-132 leads to a NAFLD-like phenotype which is antisense oligonucleotide-suppressible. Transgenic mice with inducible peripheral miRNA-132 overexpression presented increased body weight, LDL/VLDL, and triglyceride levels, an increase in hepatic pro-steatotic transcripts and a decrease in hepatic miRNA-132 targets (FIGS. 2A-H). Strikingly, diet-induced obese mice showed increased hepatic miRNA-132 in addition to hallmarks of NAFLD, and, intravenous injection of anti-miRNA-132 oligonucleotides fully reversed hepatic miRNA-132 excess and NAFLD parameters within one week, reducing hepatomegaly, triglycerides and fat vacuoles by elevation of lipolysis (FIGS. 3A-O). Moreover, knockdown of miRNA-132 in lean LDLR−/− mice, a murine model of human hyperlipidemia, reduced LDL/VLDL levels (FIGS. 6A-G).

The novel and hepatic regulatory role of miRNA-132 in lipid homeostasis uncovered by the present inventors, suggests that suppression thereof would serve as a useful therapeutic intervention in both familial and non-familial Non-Alcoholic Fatty Liver Disease (NAFLD).

Thus, according to a first aspect of the present invention there is provided a method of treating a fatty liver disease in a subject in need thereof, comprising administering to the subject a therapeutically effective amount of a polynucleotide agent which is substantially complementary to a nucleotide sequence of human miR-132.

As used herein, the term "fatty liver disease" refers to a disease or a pathological condition caused by, at least in part, abnormal hepatic lipid deposits. Fatty liver disease includes, e.g., alcoholic fatty liver disease, non-alcoholic fatty liver disease, and acute fatty liver of pregnancy. Fatty liver disease may be, e.g., macro-vesicular steatosis or micro-vesicular steatosis.

According to a particular embodiment, the disease is non-alcoholic fatty liver disease.

The non-alcoholic fatty liver disease may be a primary or a secondary non-alcoholic fatty liver disease.

The non-alcoholic fatty liver disease may be either familial (e.g. inherited liver disease due to a mutation in the LDL receptor) or non-familial.

According to a particular embodiment, the familial fatty liver disease is familial hyperlipidemia.

In some embodiment, subjects with familial hyperlipidemia have mutations in the LDLR gene that encodes the LDL receptor protein, which normally removes LDL from the circulation, or apolipoprotein B (ApoB), which is the part of LDL that binds with the receptor.

In one embodiment, the subject having the fatty liver disease has a body mass index (BMI) of less than 30.

In one embodiment, the subject having the fatty liver disease has a body mass index (BMI) of less than 25.

In yet another embodiment, the subject has no obesity-related co-morbidity.

In addition, in the present invention, non-alcoholic fatty liver disease is meant to include simple steatosis, diabetes-related liver steatosis, non-alcoholic steatohepatitis, cholestasis and liver fibrosis and liver cirrhosis which result from the progression of such diseases.

According to a particular embodiment, the subject treated for fatty liver disease does not have a neurodegenerative disease.

According to a particular embodiment, the subject treated for fatty liver disease does not have an eye disease.

According to a particular embodiment, the subject treated for fatty liver disease does not have cancer.

As mentioned, the present inventors showed that overexpression of miRNA 132 results in weight gain. Thus, the present inventors contemplate that administration of the miRNA (and not the miRNA inhibitor) can be used for the treatment of diseases associated with weight loss. Such diseases include, but are not limited to anorexia, bulimia, hyperthyroidism, body wasting associated with cancer and/or chemotherapeutic agents.

The term "microRNA", "miRNA", and "miR" are synonymous and refer to a collection of non-coding single-stranded RNA molecules of about 19-28 nucleotides in length, which regulate gene expression. miRNAs are found in a wide range of organisms and have been shown to play a role in development, homeostasis, and disease etiology.

Below is a brief description of the mechanism of miRNA activity.

Genes coding for miRNAs are transcribed leading to production of a miRNA precursor known as the pri-miRNA. The pri-miRNA is typically part of a poly-cistronic RNA comprising multiple pri-miRNAs. Alternatively, it may consist of a single gene with its own promoter, as is the case for miRNA-132 or be produced from an intron of a coding gene. The pri-miRNA may form a hairpin with a stem and loop. The stem may comprise mismatched bases.

The hairpin structure of the pri-miRNA is recognized by Drosha, which is an RNase III endonuclease. Drosha typically recognizes terminal loops in the pri-miRNA and cleaves approximately two helical turns into the stem to produce a 60-70 nucleotide precursor known as the pre-miRNA. Drosha cleaves the pri-miRNA with a staggered cut typical of RNase III endonucleases yielding a pre-miRNA stem loop with a 5' phosphate and ~2 nucleotide 3' overhang. It is estimated that approximately one helical turn of stem (~10 nucleotides) extending beyond the Drosha cleavage site is essential for efficient processing. The pre-miRNA is then actively transported from the nucleus to the cytoplasm by Ran-GTP and the export receptor Ex-portin-5.

The double-stranded stem of the pre-miRNA is then recognized by Dicer, which is also an RNase III endonuclease. Dicer may also recognize the 5' phosphate and 3' overhang at the base of the stem loop. Dicer then cleaves off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. miRNA* sequences may be found in libraries of cloned miRNAs but typically at lower frequency than the miRNAs.

Although initially present as a double-stranded species with miRNA*, the miRNA eventually becomes incorporated as a single-stranded RNA into a ribonucleoprotein complex known as the RNA-induced silencing complex (RISC). Various proteins can form the RISC, which can lead to variability in specificity for miRNA/miRNA*duplexes, binding site of the target gene, activity of miRNA (repress or activate), and which strand of the miRNA/miRNA*duplex is loaded in to the RISC.

When the miRNA strand of the miRNA:miRNA* duplex is loaded into the RISC, the miRNA* is removed and degraded. The strand of the miRNA:miRNA* duplex that is loaded into the RISC is the strand whose 5' end is less tightly paired. In cases where both ends of the miRNA:miRNA* have roughly equivalent 5' pairing, both miRNA and miRNA* may have gene silencing activity.

The RISC identifies target nucleic acids based on high levels of complementarity between the miRNA and the mRNA, especially by nucleotides 2-7 of the miRNA.

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding. Moreover, sufficient base pairing at the 3' can compensate for insufficient pairing at the 5' (Brennecke et al, 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al. (2005, Nat Genet 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut is typically between the nucleotides pairing to residues 10 and 11 of the miRNA. Alternatively, the miRNA may repress translation if the miRNA does not have the requisite degree of complementarity to the miRNA. Translational repression may be more prevalent in animals since animals (compared to humans) may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA*may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

The term "microRNA mimic" or "miRNA mimic" refers to synthetic non-coding RNAs that are capable of entering the RNAi pathway and regulating gene expression. miRNA mimics imitate the function of endogenous miRNAs and can be designed as mature, double stranded molecules or mimic precursors (e.g., or pre-miRNAs). miRNA mimics can be comprised of modified or unmodified RNA, DNA, RNA-DNA hybrids, or alternative nucleic acid chemistries (e.g., LNAs or 2'-O,4'-C-ethylene-bridged nucleic acids (ENA)). For mature, double stranded miRNA mimics, the length of the duplex region can vary between 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA. The sequence of the miRNA may comprise the sequence as set forth in SEQ ID NO: 9 or variants thereof.

Preparation of miRNAs mimics can be effected by any method known in the art such as chemical synthesis or recombinant methods.

It will be appreciated from the description provided herein above that contacting cells with a miRNA may be effected by transfecting the cells with e.g. the mature double stranded miRNA, the pre-miRNA or the pri-miRNA.

The pre-miRNA sequence may comprise from 45-90, 60-80 or 60-70 nucleotides.

The pri-miRNA sequence may comprise from 45-30,000, 50-25,000, 100-20,000, 1,000-1,500 or 80-100 nucleotides.

Since the present inventors showed that overexpression of miRNA 132 results in weight gain, the present inventors further contemplate use of miRNA 132 inhibitors for treating obesity and lowering body weight.

Thus, according to another aspect of the present invention there is provided a method of treating obesity in a subject in need thereof, comprising administering to the subject a therapeutically effective amount of a polynucleotide agent which is substantially complementary to a nucleotide sequence of human miR-132, thereby treating the obesity in the subject.

According to one embodiment the obese subject has a body mass index (BMI) of greater than 30. Subjects having BMI between 25 and 30 are considered overweight and in one embodiment, are treated by the agents disclosed herein. The body mass index (BMI) is calculated by dividing an individual's weight in kilograms by the square of their height in meters. BMI does not distinguish fat mass from lean mass and an obese subject typically has excess adipose tissue.

Thus, in one embodiment of the present invention, the obese subject has a BMI greater than 30. In one embodiment, the subject has a BMI of 25 or over, e.g. 26, 27, 28, 29, 30, 31, 32, 33, 34, 35, 36, 37, 38, 39 or 40 or greater and has no obesity-related co-morbidity. In one embodiment, the patient is morbidly obese and has a BMI of 40 or over. In one embodiment, the subject is obese and/or suffering from complications associated with obesity. In one embodiment, the subject is obese and/or was suffering from complications associated with obesity, which have now been corrected. In one embodiment, the subject has a Body Mass Index (BMI) of over 25, and preferably over 30.

According to a particular embodiment, the subject treated obesity does not have a neurodegenerative disease.

According to a particular embodiment, the subject treated obesity does not have an eye disease.

According to a particular embodiment, the subject treated for obesity does not have cancer.

It will be appreciated that for the treatment of obesity, care should be taken for the formulation of the polynucleotide agents, such that they do not accumulate in the liver and have a local effect.

As used herein the term miRNA-132 refers to the RNA comprising a nucleic acid sequence as set forth in SEQ ID NO: 9 (UAACAGUCUACAGCCAUGGUCG).

In some embodiments, the miR-132 inhibitor of this aspect of the present invention is an antagomir. An "antagomir" refers to a single stranded, double stranded, partially double stranded or hairpin structured oligomer or polymer of ribonucleic acid (RNA) or deoxyribonucleic acid (DNA) or both or modifications thereof, which is antisense with respect to its miRNA target.

Examples of antagomirs and other miRNA inhibitors are described in WO2009/20771, WO2008/91703, WO2008/046911, WO2008/074328, WO2007/90073, WO2007/27775, WO2007/27894, WO2007/21896, WO2006/93526, WO2006/112872, WO2007/112753, WO2007/112754, WO2005/23986, or WO2005/13901, all of which are hereby incorporated by reference.

Custom designed Anti-miR molecules are commercially available from Applied Biosystems. Thus, in some embodiments, the antagomir is an Ambion anti-miR inhibitor. These molecules are chemically modified and optimized single-stranded nucleic acids designed to specifically inhibit naturally occurring mature miRNA molecules in cells.

Custom designed Dharmacon Meridian microRNA Hairpin Inhibitors are also commercially available from Thermo Scientific. These inhibitors include chemical modifications and secondary structure motifs. For example, Vermeulen et al. reports in U.S. Patent Publication 2006/0223777 the identification of secondary structural elements that enhance the potency of these molecules. Specifically, incorporation of highly structured, double-stranded flanking regions around the reverse complement core significantly increases inhibitor function and allows for multi-miRNA inhibition at sub-nanomolar concentrations. Other such improvements in antagomir design are contemplated for use in the disclosed methods.

In preferred embodiments, the disclosed antagomir includes a region of sufficient nucleotide length and sufficient complementarity to miR-132 that the antagomir forms a duplex with miR-132. Given the sequence of miR-132, an antagomir can be designed according to the rules of Watson and Crick base pairing.

Thus, the antagomir can be an antisense oligonucleotide having a single-stranded nucleic acid sequence that is complementary to at least 8, 9, 10, 11, 12, 13, 14, 15, 16, 17, 18, 19, 20, 21, 22, 23 or 24 contiguous nucleotides in miR-132, wherein the antisense oligonucleotide forms a duplex with miR-132 under physiological conditions. In certain embodiments, the single-stranded nucleic acid sequence hybridizes under stringent conditions to an oligonucleotide having the sequence of SEQ ID NO:9.

In preferred embodiments, the antisense oligonucleotide contains one or more nucleotide modifications that increase stability of the antisense oligonucleotide in the presence of a nuclease. For example, one or more of the nucleotide units of the antisense oligonucleotide can be locked nucleic acid (LNA) units. In some embodiments, one or more of the nucleotide units of the antisense oligonucleotide are 2' substituted nucleotide analogues. Additionally, one or more of the inter-nucleoside linkages between the nucleotide units of the antisense oligonucleotide can be phosphorothioate inter-nucleoside linkages. It is understood that the antisense oligonucleotide can include one or more different types of modifications. Thus, the antisense oligonucleotide can have LNA units, 2' substituted nucleotide analogues, and phosphorothioate inter-nucleoside linkages. Other modifications that are suitable for improving therapeutic use of a nucleic acid, such as an RNA molecule, can also be used with the disclosed antisense oligonucleotide.

1. Length: The antagomir can include an antisense oligonucleotide having a length of at least 8 contiguous nucleotides. Therefore, the antisense oligonucleotide can have 8, 9, 10, 11, 12, 13, 14, 15, 16, 17, 18, 19, 20, 21, 22, 23, or 24 contiguous nucleotides. The oligonucleotide is preferably less than 30 contiguous nucleotides in length. The oligonucleotide can be less than 25, 26, 27, 28, 29, 30, 31, 32, 33, 34, 35, 36, 37, 38, 39, 40 contiguous nucleotides in length.

2. Complementarity: The disclosed antagomir can include an antisense oligonucleotide having a region that is at least partially, and in some embodiments fully, complementary to miR-132. It is not necessary that there be perfect complementarity between the antagomir and the target, but the correspondence must be sufficient to enable the antisense oligonucleotide to duplex with miR-132 and subsequently reduce its activity.

The disclosed antagomir can include an antisense oligonucleotide having a region that is at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% complementary to miR-132.

Preferably, the disclosed antagomir has at least 6, 7, 8, 9, 10, 11, 12, 13, 14, 15, 16, 17, 18, 19, 20 or more contiguous nucleotides complementary to an miR-132 nucleotide sequence. In one embodiment, the disclosed antagomir has a nucleotide sequence that is complementary to miR-132. Thus, in one embodiment, the disclosed antagomir has at least 6, 7, 8, 9, 10, 11, 12, 13, 14, 15, 16, 17, 18, 19, 20 or more contiguous nucleotides that are complementary to miR-132.

In some embodiments, there will be nucleotide mismatches in the region of complementarity. In a preferred embodiment, the region of complementarity will have no more than 1, 2, 3, 4, or 5 mismatches.

In some embodiments, the antagomir is "exactly complementary" to miR-132. Thus, in one embodiment, the antagomir can anneal to miR-132 to form a hybrid made exclusively of Watson-Crick base pairs in the region of exact complementarity. Thus, in some embodiments, the antagomir specifically discriminates a single-nucleotide difference. In this case, the antagomir only inhibits miR-132 activity if exact complementarity is found in the region of the single-nucleotide difference.

3. Modifications: The disclosed antagomirs and miRNAs include oligomers or polymers of ribonucleic acid (RNA) or deoxyribonucleic acid (DNA) or both or modifications thereof. This term includes oligonucleotides composed of naturally occurring nucleobases, sugars, and covalent internucleoside (backbone) linkages as well as oligonucleotides having non-naturally-occurring portions that operate similarly. Such modified or substituted oligonucleotides are often preferred over native forms because of desirable properties such as, for example, enhanced cellular uptake, enhanced affinity for nucleic acid targets, and/or increased stability in the presence of nucleases.

The disclosed polynucleotide agents can include unmodified RNA and DNA as well as RNA and DNA that have been modified, e.g., to improve efficacy, and polymers of nucleoside surrogates. "Unmodified" RNA refers to a molecule in which the components of the nucleic acid, namely sugars, bases, and phosphate moieties, are the same or essentially the same as those that occur in nature, preferably as occurs naturally in the human body. "Modified" RNA, as used herein, refers to a molecule where one or more of the components of the nucleic acid, namely sugars, bases, and phosphate moieties, are different from that which occurs in nature, preferably different from that which occurs in the human body. While they are referred to as "modified RNAs" they will of course, because of the modification, include molecules that are not, strictly speaking, RNAs.

The disclosed polynucleotide agents can be modified to enhance resistance to nucleases. The disclosed polynucleotide agents can include nucleotide modifications that stabilized it against nucleolytic degradation. The oligomer can be a totalmer, mixmer, gapmer, tailmer, headmer or blockmer. A "totalmer" is a single stranded oligonucleotide that only comprises non-naturally occurring nucleotides.

The term "gapmer" refers to an oligonucleotide composed of modified nucleic acid segments flanking at least 5 naturally occurring nucleotides (i.e., unmodified nucleic acids).

The term "blockmer" refers to a central modified nucleic acid segment flanked by nucleic acid segments of at least 5 naturally occurring nucleotides.

The term "tailmer" refers to an oligonucleotide having at least 5 naturally occurring nucleotides at the 5'-end followed by a modified nucleic acid segment at the 3'-end.

The term "headmer" refers to oligonucleotide having a modified nucleic acid segment at the 5'-end followed by at least 5 naturally occurring nucleotides at the 3'-end.

The term "mixmer" refers to an oligonucleotide that comprises both naturally and non-naturally occurring nucleotides. However, unlike gapmers, tailmers, headmers and blockmers, there is no contiguous sequence of more than 5 naturally occurring nucleotides, such as DNA units.

Modified nucleic acids and nucleotide surrogates can include one or more of (i) replacement of one or both of the non-linking phosphate oxygens and/or of one or more of the linking phosphate oxygens; (ii) replacement of a constituent of the ribose sugar, e.g., of the 2' hydroxyl on the ribose sugar, or wholesale replacement of the ribose sugar with a structure other than ribose; (iii) wholesale replacement of the phosphate moiety with "dephospho" linkers; (iv) modification or replacement of a naturally occurring base; (v) replacement or modification of the ribose-phosphate backbone; or (vi) modification of the 3' end or 5' end of the RNA, e.g., removal, modification or replacement of a terminal phosphate group or conjugation of a moiety, such as a fluorescently labeled moiety, to either the 3' or 5' end of RNA.

The phosphate group in a nucleic acid can be modified by replacing one of the oxygen atoms with a different substituent. One result of this modification to RNA phosphate backbones can be increased resistance of the oligoribonucleotide to nucleolytic breakdown. Thus, it can be desirable in some embodiments to introduce alterations that result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur.

The phosphate linker can also be modified by replacement of a linking oxygen with nitrogen (bridged phosphoroamidates), sulfur (bridged phosphorothioates) and carbon (bridged methylenephosphonates). The replacement can occur at a terminal oxygen.

The phosphate group can be replaced by non-phosphorus containing connectors. Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methylenecarbonylamino and methylenemethylimino groups.

A modified RNA can include modification of all or some of the sugar groups of the ribonucleic acid. For example, the 2' hydroxyl group (OH) can be modified or replaced with a number of different "oxy" or "deoxy" substituents.

Examples of "oxy"-2' hydroxyl group modifications include alkoxy or aryloxy (OR, e.g., R.dbd.H, alkyl, cycloalkyl, aryl, aralkyl, heteroaryl or sugar); polyethyleneglycols (PEG), O(CH.sub.2CH.sub.2O).sub.nCH.sub.2CH.sub.2OR; "locked" nucleic acids (LNA) in which the 2' hydroxyl is connected, e.g., by a methylene bridge, to the 4' carbon of the same ribose sugar; amine, O-AMINE and aminoalkoxy, O(CH.sub.2),AMINE, (e.g., AMINE=NH.sub.2; alkylamino, dialkylamino, heterocyclyl amino, arylamino, diaryl amino, heteroaryl amino, or diheteroaryl amino, ethylene diamine, polyamino). Oligonucleotides containing only the methoxyethyl group (MOE) (OCH.sub.2CH.sub.2OCH.sub.3, a PEG derivative) exhibit nuclease stabilities comparable to those modified with the robust phosphorothioate modification.

"Deoxy" modifications include hydrogen (i.e., deoxyribose sugars); halo (e.g., fluoro); amino (e.g. NH.sub.2; alkylamino, dialkylamino, heterocyclyl, arylamino, diaryl amino, heteroaryl amino, diheteroaryl amino, or amino acid); NH(CH.sub.2CH.sub.2NH).sub.nCH.sub.2CH.sub.2-AMINE (AMINE=NH.sub.2; alkylamino, dialkylamino, heterocyclyl amino, arylamino, diaryl amino, heteroaryl amino, or diheteroaryl amino), —NHC(O)R(R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality.

Thus, the disclosed polynucleotide agents can include a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In some embodiments, the antagomir includes at least one 2'-O-methyl-modified nucleotide, and in some embodiments, all of the nucleotides of the antagomir include a 2'-O-methyl modification.

The sugar group can also contain one or more carbons that possess the opposite stereochemical configuration than that of the corresponding carbon in ribose. Thus, a modified RNA can include nucleotides containing e.g., arabinose, as the sugar.

Modified RNAs can also include "abasic" sugars, which lack a nucleobase at C-1'. These abasic sugars can also further contain modifications at one or more of the constituent sugar atoms. The modification can also entail the wholesale replacement of a ribose structure with another entity (an SRMS) at one or more sites in the oligonucleotide agent.

The 3' and 5' ends of an oligonucleotide can be modified. Such modifications can be at the 3' end, 5' end, or both ends of the molecule. They can include modification or replacement of an entire terminal phosphate or of one or more of the atoms of the phosphate group. For example, the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a spacer. The terminal atom of the spacer can connect to or replace the linking atom of the phosphate group or the C-3' or C-5'0, N, S or C group of the sugar. Alternatively, the spacer can connect to or replace the terminal atom of a nucleotide surrogate (e.g., PNAs). These spacers or linkers can include e.g., —(CH$_2$)$_n$-, —(CH$_2$)$_n$N—, —(CH$_2$)$_n$O—, —(CH$_2$)$_n$S—, O(CH$_2$CH$_2$O)$_n$CH$_2$CH$_2$OH (e.g., n=3 or 6), abasic sugars, amide, carboxy, amine, oxyamine, oxyimine, thioether, disulfide, thiourea, sulfonamide, or morpholino, or biotin and fluorescein reagents.

Other examples of terminal modifications include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid,O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles).

Terminal modifications include the addition of a methylphosphonate at the 3'-most terminal linkage; a 3' C5-aminoalkyl-dT; 3' cationic group; or another 3' conjugate to inhibit 3'-5' exonucleolytic degradation.

Terminal modifications useful for modulating activity include modification of the 5' end with phosphate or phosphate analogs. For example, in some embodiments, oligonucleotide agents are 5' phosphorylated or include a phosphoryl analog at the 5' terminus. 5'-phosphate modifications include those which are compatible with RISC mediated gene silencing. Suitable modifications include: 5'-monophosphate ((HO)$_2$(O)P—O-5'); 5'-diphosphate ((HO)$_2$(O)P—O—P(HO)(O)—O-5'); 5'-triphosphate ((HO)$_2$(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)$_2$(S)P—O-5'); 5'-monodithiophosphate (phosphorodithioate; (HO)(HS)(S)P—O-5'), 5'-phosphorothiolate ((HO)$_2$(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)$_2$(O)P—NH-5', (HO)(NH$_2$)(O)P—O-5'), 5'-alkylphosphonates (R=alkyl-methyl, ethyl, isopropyl, propyl, etc., e.g. RP(OH)(O)—O-5'-, (OH)$_2$(O)P-5'-CH$_2$-), 5'-alkyletherphosphonates (R=alkylether=methoxymethyl (MeOCH$_2$-), ethoxymethyl, etc., e.g. RP(OH)(O)—O-5'-).

Adenine, guanine, cytosine and uracil are the most common bases found in RNA. These bases can be modified or replaced to provide RNAs having improved properties. For example, nuclease resistant oligonucleotides (i.e., oligoribonucleotides) can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases, e.g., "unusual bases" and "universal bases", can be employed. Examples include 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynyleytosine, dihydrouracil, 3-deaza-5-azacytosine, 2-aminopurine, 5-alkyluracil, 7-alkylguanine, 5-alkyl cytosine,7-deazaadenine, N6, N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, N$^4$-acetyl cytosine, 2-thiocytosine, N6-methyladenine, N6-isopentyladenine, 2-methylthio-N6-isopentenyladenine, N-methylguanines, or O-alkylated bases.

The disclosed polynucleotide agents can include an internucleotide linkage (e.g., the chiral phosphorothioate linkage) useful for increasing nuclease resistance.

Phosphorothioates (or S-oligos) are a variant of normal DNA or RNA in which one of the nonbridging oxygens is replaced by a sulfur. The sulfurization of the internucleotide bond dramatically reduces the action of endo- and exonucleases including 5' to 3' and 3' to 5' DNA POL 1 exonuclease, nucleases S1 and P 1, RNases, plasma nucleases and snake venom phosphodiesterase. In addition, the potential for crossing the lipid bilayer increases. Because of these important improvements, phosphorothioates have found increasing application in cell regulation.

Phosphorothioates are made by two principal routes: by the action of a solution of elemental sulfur in carbon disulfide on a hydrogen phosphonate, or by the more recent method of sulfurizing phosphite triesters with either tetraethylthiuram disulfide (TETD) or 3H-1,2-bensodithiol-3-one 1,1-dioxide (BDTD).

One way to increase resistance is to identify cleavage sites and modify such sites to inhibit cleavage. For example, the dinucleotides 5'-UA-3',5'-UG-3',5'-CA-3',5'-UU-3', or 5'-CC-3' can serve as cleavage sites. Enhanced nuclease resistance can therefore be achieved by modifying the 5' nucleotide, resulting, for example, in at least one 5'-uridine-adenine-3' (5'-UA-3') dinucleotide wherein the uridine is a 2'-modified nucleotide; at least one 5'-uridine-guanine-3' (5'-UG-3') dinucleotide, wherein the 5'-uridine is a 2'-modified nucleotide; at least one 5'-cytidine-adenine-3' (5'-CA-3') dinucleotide, wherein the 5'-cytidine is a 2'-modified nucleotide; at least one 5'-uridine-uridine-3' (5'-UU-3') dinucleotide, wherein the 5'-uridine is a 2'-modified nucleotide; or at least one 5'-cytidine-cytidine-3' (5'-CC-3') dinucleotide, wherein the 5'-cytidine is a 2'-modified nucleotide. Thus, the disclosed polynucleotide agents can include at least 2, 3, 4 or 5 of such dinucleotides. In certain embodiments, all the pyrimidines of an antagomir carry a 2'-modification, and the disclosed polynucleotide agents therefore have enhanced resistance to endonucleases.

An antagomir can have secondary structure, but it is preferably substantially single-stranded under physiological conditions at least in the region of the antagomir that is complementary to the miRNA. An antagomir that is substantially single-stranded is single-stranded to the extent that less than about 50% (e.g., less than about 40%, 30%, 20%, 10%, or 5%) of the antagomir is duplexed with itself. Thus, the antagomir preferably does not form hairpin loops, bulges or internal loops within the complementary region under physiological conditions.

In a preferred embodiment, the antagomir does not include a sense strand. In some embodiments, the antagomir is partially double-stranded but is single-stranded at least in the region of the antagomir that is complementary to the miRNA. The term "partially double-stranded" refers to double stranded structures wherein one strand contains fewer nucleotides than its complementary strand. In general, such partial double stranded agents will have less than 75% double stranded structure, preferably less than 50%, and more preferably less than 25%, 20% or 15% double stranded structure.

In a preferred embodiment, the polynucleotide agent is suitable for delivery to a cell in vivo, e.g., to a cell in an organism. In another embodiment, the polynucleotide agent is suitable for delivery to a cell in vitro, e.g., to a cell in a cell line in culture or a suspension. The polynucleotide agent can include a ligand that is selected to improve stability, distribution or cellular uptake of the agent. For example, the ligand can be a lipophilic moiety, e.g., cholesterol, which enhances entry of the polynucleotide agent into a cell.

The polynucleotide agent can also be encapsulated by cationic lipid particles. Cationic lipid saturation influences intracellular delivery of encapsulated nucleic acids. Cationic lipids include 1,2-distearyloxy-N,N-dimethyl-3-aminopropane (DSDMA), 1,2-dioleyloxy-N,N-dimethyl-3-aminopropane (DODMA), 1,2-dilinoleyloxy-N,N-dimethyl-3-aminopropane (DLinDMA) and 1,2-dilinolenyloxy-N,N-dimethyl-3-aminopropane (DLenDMA).

In some embodiments, the disclosed polynucleotide agents can include an aminoglycoside ligand, which can cause the antagomir to have improved hybridization properties or improved sequence specificity. Exemplary aminoglycosides include glycosylated polylysine; galactosylated polylysine; neomycin B; tobramycin; kanamycin A; and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. In some embodiments the guanidine analog (the guanidinoglycoside) of an aminoglycoside ligand is tethered to an oligonucleotide agent. In a guanidinoglycoside, the amine group on the amino acid is exchanged for a guanidine group. Attachment of a guanidine analog can enhance cell permeability of an oligonucleotide agent.

The disclosed polynucleotide agents can be expressed within cells from an expression vector having a nucleic acid encoding the polynucleotide agent. The nucleic acid sequence can be operably linked to an expression control sequence, such as a promoter. Those skilled in the art realize that any nucleic acid can be expressed in eukaryotic cells from the appropriate DNA/RNA vector.

Thus, the disclosed polynucleotide agents can be expressed from transcription units inserted into DNA or RNA vectors. The recombinant vectors can be DNA plasmid or viral vectors. Oligonucleotide agent-expressing viral vectors can be constructed based on, but not limited to, adeno-associated virus, retrovirus, lentivirus, adenovirus, or alphavirus. The recombinant vectors capable of expressing the oligonucleotide agents can be delivered as described above, and can persist in target cells. Alternatively, viral vectors can be used that provide for transient expression of nucleic acid molecules. Such vectors can be repeatedly administered as necessary. Once expressed, the disclosed antagomir interacts with miR-132 and inhibits its activity. In preferred embodiments, the at least part of the antagomir forms a duplex with endogenous miR-132, which prevents the endogenous miR-132 from binding to its target mRNA (e.g., FoxO3, Pten, Sirt1, P300 and Cyp2e1), which results in increased translation of the target mRNA. Delivery of oligonucleotide agent-expressing vectors can be systemic, such as by intravenous or intramuscular administration, by administration to target cells ex-planted from a subject followed by reintroduction into the subject, or by any other means that would allow for introduction into the desired target cell (for a review see Couture et al., Trends in Genetics 12:510, 1996).

According to a specific embodiment, the antagomir of this aspect of the invention comprises at least 15 consecutive bases of SEQ ID NO: 8.

According to a specific embodiment, the antagomir of this aspect of the invention comprises the sequence as set forth in SEQ ID NO: 7.

According to a specific embodiment, the antagomir of this aspect of the invention consists of the sequence as set forth in SEQ ID NO: 7.

In another embodiment, the antagomir (e.g. SEQ ID NO: 7) has a 2-O-methyl and fully phosphorothioated backbone.

In another embodiment, the antagomir comprises locked nucleic acids (LNAs). In one embodiment, the antagomir (e.g. SEQ ID NO: 7) comprises LNAs. In another embodiment, the antagomir (e.g. SEQ ID NO: 10) comprises LNAs in a pattern as set forth in SEQ ID NO: 11.

The polynucleotide agents disclosed herein can be administered per se or as part of a pharmaceutical composition.

Methods for preparing pharmaceutical compositions are within the skill in the art, for example as described in Remington's Pharmaceutical Science, 18th ed., Mack Publishing Company, Easton, Pa. (1990), and The Science and Practice of Pharmacy, 2003, Gennaro et al.

In one embodiment, the formulations include the polynucleotide agents e.g. antagomir (e.g., 0.1 to 90% by weight), or a physiologically acceptable salt thereof, mixed with a physiologically acceptable carrier medium. Preferred physiologically acceptable carrier media are water, buffered water, normal saline, 0.4% saline, or 0.3% glycine, for injection.

The pharmaceutical formulations can also include conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (e.g., calcium DTPA, CaNaDTPA-bisamide), or, optionally, additions of calcium or sodium salts (for example, calcium chloride, calcium ascorbate, calcium gluconate or calcium lactate). Pharmaceutical compositions can be packaged for use in liquid form, or can be lyophilized.

For solid compositions, conventional non-toxic solid carriers can be used; for example, pharmaceutical grades of mannitol, lactose, starch, magnesium stearate, sodium saccharin, talcum, cellulose, glucose, sucrose, magnesium carbonate, and the like. For example, a solid pharmaceutical composition for oral administration can include any of the carriers and excipients listed above and 10-95%, preferably 25%-75%, of one or more single-stranded oligonucleotide agents.

A formulated compound may assume a variety of states. In some examples, the composition is at least partially crystalline, uniformly crystalline, and/or anhydrous (e.g., less than 80, 50, 30, 20, or 10% water). In another example, the polynucleotide agent e.g. antagomir is in an aqueous phase, e.g., in a solution that includes water, this form being the preferred form for administration via inhalation.

The polynucleotide agents can be incorporated into a delivery vehicle, e.g., a liposome (particularly for the aqueous phase), or a particle (e.g., a microparticle). Generally, the compound is formulated in a manner that is compatible with the intended method of administration.

The polynucleotide formulations can include liposomes, such as surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated polynucleotide agents.

Long-circulating liposomes enhance the pharmacokinetics and pharmacodynamics of DNA and RNA, particularly compared to conventional cationic liposomes which are known to accumulate in tissues of the MPS. Long-circulating liposomes are also likely to protect drugs from nuclease degradation to a greater extent compared to cationic liposomes, based on their ability to avoid accumulation in metabolically aggressive MPS tissues such as the liver and spleen.

The types of pharmaceutical excipients that are useful as carrier include stabilizers such as human plasma albumin (HSA), bulking agents such as carbohydrates, amino acids and polypeptides; pH adjusters or buffers; salts such as sodium chloride; and the like. These carriers may be in a crystalline or amorphous form or may be a mixture of the two. Bulking agents that are particularly valuable include compatible carbohydrates, polypeptides, amino acids or combinations thereof. Suitable carbohydrates include monosaccharides such as galactose, D-mannose, and sorbose; disaccharides, such as lactose and trehalose; cyclodextrins, such as 2-hydroxypropyl.beta.-cyclodextrin; and polysaccharides, such as raffinose, maltodextrins, and dextrans; alditols, such as mannitol and xylitol. A preferred group of carbohydrates includes lactose, threhalose, raffinose maltodextrins, and mannitol.

Combinations:

The polynucleotide agent can be formulated in combination with another agent, e.g., another therapeutic agent or an agent that stabilizes an oligonucleotide agent, e.g., a protein that complexes with the oligonucleotide agent. Still other agents include chelators, e.g., EDTA (e.g., to remove divalent cations such as $Mg^{2+}$), salts, and RNAse inhibitors (e.g., a broad specificity RNAse inhibitor such as RNAsin). In one embodiment, the antagomir preparation includes another antagomir, e.g., a second antagomir that can down-regulate expression of a second miRNA. In some embodiments, the agents are directed to the same target nucleic acid but different target sequences. In another embodiment, each antagomir is directed to a different target. In another embodiment the other agent down-regulates an amount or an activity of FoxO3, Pten, P300 and/or Sirt1 (e.g. siRNA, antisense etc).

The polynucleotide agent can be formulated in combination with one or more other compounds, especially other compounds involved in inhibition of cholesterol synthesis or uptake (i.e. an anti-lipid agent), such as a statin, bile acid sequestrants, cholesterol absorption inhibitors such as fibrate, nicotinic acid.

Other examples of anti-lipid agents include, but are not limited to an phosphodiesterase inhibitor, an adenylate cyclase activator, a lipolysis stimulator, a beta-adrenergic receptor agonist, an alpha-2-adrenergic receptor antagonist, and combinations thereof.

In another embodiment, the at least one other anti-lipid agent comprises at least one agent selected from the group consisting of a xanthine analog, forskolin, a Coleus forskohlii extract, a hawthorne extract, a cola extract, isoproterenol, yohimbine, Ginkgo biloba extract, perilla oil, and combinations thereof.

Alternatively, the polynucleotide agents can be packaged in an article of manufacture which comprises one or more other compound as described herein above (e.g. anti-lipid agent) in a separate packaging.

Methods of Administration:

The polynucleotide agents of the present invention may be administered in a number of ways depending upon whether local or systemic treatment is desired and upon the area to be treated. Administration may be topical (including ophthalmic, intranasal, transdermal, intrapulmonary), oral or parenteral. Parenteral administration includes intravenous drip, subcutaneous, intraperitoneal or intramuscular injection, or intrathecal or intraventricular administration.

Nucleic acid molecules can be administered to cells by a variety of methods known to those of skill in the art, including, but not restricted to, encapsulation in liposomes, by ionophoresis, or by incorporation into other vehicles, such as hydrogels, biodegradable nanocapsules, and bioadhesive microspheres, or by proteinaceous vectors.

The polynucleotide agents (e.g. antagomir) can be administered to the subject either as a naked oligonucleotide agent, in conjunction with a delivery reagent, or as a recombinant plasmid or viral vector which expresses the oligonucleotide agent.

The polynucleotide agent composition can be administered to the subject by any means suitable for delivering the agent to the cells of the tissue at or near the area of unwanted miR-132 expression (e.g. the liver). Exemplary delivery methods include administration by gene gun, electroporation, or other suitable parenteral administration route.

Suitable parenteral administration routes include intravascular administration (e.g., intravenous bolus injection, intravenous infusion, intra-arterial bolus injection, intra-arterial infusion and catheter instillation into the vasculature); peri- and intra-tissue injection (e.g., intraocular injection, intra-retinal injection, or sub-retinal injection); subcutaneous injection or deposition including subcutaneous infusion (such as by osmotic pumps); direct application by a catheter or other placement device (e.g., an implant comprising a porous, non-porous, or gelatinous material).

The polynucleotide agents of the invention can be provided in sustained release composition. The use of immediate or sustained release compositions depends on the nature of the condition being treated. If the condition consists of an acute or over-acute disorder, treatment with an immediate release form will be preferred over a prolonged release composition. Alternatively, for certain preventative or long-term treatments, a sustained release composition may be appropriate.

The polynucleotide agents of the invention can be administered in a single dose or in multiple doses. Where the administration of the polynucleotide is by infusion, the infusion can be a single sustained dose or can be delivered by multiple infusions.

The polynucleotide agent can be administered to the patient in a dose or doses of about or of at least about 0.005, 0.05, 0.5, 1, 5, 10, 15, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 mu·g, ng, or mg, or more, or any range derivable therein. Alternatively, the amount specified may be the amount administered as the average daily, average weekly, or average monthly dose, or it may be expressed in terms of mg/kg, where kg refers to the weight of the patient and the mg is specified above. In other embodiments, the amount specified is any number discussed above but expressed as mg/m.sup.2 (with respect to tissue size or patient surface area).

The dose of the polynucleotide agent is not particularly limited. For example, it is approximately 0.1 ng to approximately 100 mg/kg/day, and preferably approximately 1 ng to approximately 10 mg/kg/day. In general, the effects of miRNA appear 1 to 3 days after the administration. Thus, it is preferable that the agent be administered at a frequency of daily to once every three days. When an expression vector is used, administration can be carried out approximately once in a week.

In certain embodiments, the compositions of the present invention may comprise, for example, at least about 0.1% of an active compound (i.e. polynucleotide agent). In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Constitutive miRNA-132 Overexpressing Mice:

Constitutive miRNA-132 transgenic mice were generated by microinjection of a fragment miRNA-132 expression vector obtained from GeneCopoeia (Germantown, Md. USA), which was linearized using SfiI and ClaI to produce a 902 base-pair sequence, injected to CB6/F1 E0.5 zygotes, and transplanted to ICR pseudo-pregnant females. PCR was performed on P21, E10.5 and E14.5 using the following primers: forward: GGAATCGCGGGCCCAGTGTC (SEQ ID NO: 1), reverse: GGGCGGAGAATGGGCGGAAC (SEQ ID NO: 2).

Inducible miRNA-132 Overexpressing Mice:

Inducible miRNA-132 transgenic mice were generated by cloning the mouse miRNA-132 precursor sequence into the EcoRI and XbaI sites of the pTRE-tight plasmid (Clontech, Calif., USA). The Vector was linearized using XhoI sites and a 735 base-pair sequence was microinjected to CB6/F1 E0.5 zygotes, and transplanted to ICR pseudo-pregnant females. 6 Transgenic founders were generated and crossed with the reverse tetracycline controlled trans-activator (rtTA) followed by a β-globin poly A which was inserted downstream of the Gt (ROSA) 26Sor promoter and the ColA1 locus, B6.Cg-Gt(ROSA)26Sor$^{tm1(rtTA*M2)Jae}$/J obtained from the Jackson Laboratory (ME, USA). MiRNA-132 expression was validated using microRNA quantification system (Quanta Biosciences, MD, USA). The highest expressing line was selected out of the 6 lines. To induce expression of miRNA-132, 2 mg/ml Doxycycline (Sigma-Aldrich, Israel) and 10 mg/ml sucrose were added to the drinking water, and changed every 3 days for 14 days. Mice were group housed, at a constant temperature (22±1° C.) and 12-h light/dark cycles.

Mice Genotyping:

pTRE-miR-132xrtTA mice were genotyped for the miRNA-132 transgene using nested quantitative real-time PCR. The initial PCR step was performed using the following primers: forward: TACTGTGGGAACCGGAGGTA (SEQ ID NO: 3), reverse: TGAAATTTGTGATGCTATT- GCTTT (SEQ ID NO: 4). PCR product levels were determined by quantitative real-time reverse transcriptase (ABI prism 7900HT, SYBR green master mix, Applied Biosystems, CA, USA) using the primers: forward: ACAGTCTACAGCCATGGTCGC (SEQ ID NO: 5), reverse: CGCTCTGTATCTGCCCAAACC (SEQ ID NO: 6).

LDLR−/− Mice:

9-10 week old LDLR knockout mice (LDLR−/−, stock number: 002207, Jackson Laboratories, USA) were fed with regular chow diet (TD-2918, Harlan Teklad, Israel) which consists of 18% of fat calories, and has 24% and 58% of calories derived from protein and carbohydrates, respectively (energy density of 3.1 kcal/g). LDLR−/− were injected intravenously with 3-successive daily injections of 3.3 mg/kg of an LNA oligonucleotide complementary to mature miRNA-132 (AM132) or a control sequence of anti-miRNA-608 (AM608) that is primate-specific (Exiqon, Vedbaek, Denmark). Mice were sacrificed 7 days post treatment and blood and tissue samples were collected.

Diet:

Inducible miRNA-132 transgenic mice and C57Bl/6j control mice (Harlan, Israel) were fed with regular chow diet (RCD; TD-2918, Harlan Teklad, Israel) which consists of 18% of fat calories, and has 24% and 58% of calories derived from protein and carbohydrates, respectively (energy density of 3.1 kcal/g). In other experiments, C57Bl/6j mice were fed with high-fat diet (HFD; TD-97070, Harlan Teklad, Wis., USA) which consists of 59.9% of fat calories, and has 18.8% and 21.3% of calories derived from protein and carbohydrates, respectively (energy density of 5.1 kcal/g). The fatty acid profile (% of total fat): 45% saturated, 24% trans, 24% monounsaturated (cis), 7% polyunsaturated (cis).

Oligonucleotides:

DIO C57bl/6 J mice after 9 or 11 weeks of HFD (18 week-old) or age-matched controls in case of RCD fed mice, were injected intravenously with 3-successive daily injections or a single day injection of 3.3 mg/kg (unless otherwise noted) of an LNA oligonucleotide complementary to mature miRNA-132 (AM132) (SEQ ID NO: 7) or a control sequence of anti-miRNA-608 (AM608) that is primate-specific (Exiqon, Vedbaek, Denmark) or DDW. 9-week old wild type C57Bl/6J mice fed with regular chow were used for testing the effect of AM132 on lean mice, and were sacrificed 2 weeks post treatment. 2-O-methyl protected oligonucleotides had full-length phosphorothioate backbones (Sigma-Aldrich Israel). Mice were sacrificed at different time points and blood and tissue samples were collected. LNA GapmeRs designed for selected targets (Exiqon, Vedbaek, Denmark) were injected intravenously at a dose of 10 mg/kg and sacrificed 7 days post treatment.

Glucose Metabolism Experiments:

Glucose Tolerance Tests (GTT):

For intraperitoneal GTT (IP-GTT) mice fasted for 18 hours and were then injected with 10% glucose (D-glucose, Sigma, St. Louis, Mo.) in water for injection (Brown) at a 1 mg/kg dose. Mice were bled from a tail clip. Blood glucose was measured before injection (time 0) and 15, 30, 60, 90 and 120 min after injection using a handheld glucometer.

Insulin Tolerance Tests (ITT):

For intraperitoneal ITT (IP-ITT) mice fasted for 4 hours and were then injected with insulin (Biological industries, 01-818-1H) in phosphate buffered saline at a 0.75 U/kg dose. Mice were bled from a tail clip. Blood glucose was measured before injection (time 0) and 15, 30, 60, 90 and 120 min after injection using a handheld glucometer.

Insulin ELISA:

Fasting serum insulin was determined using enzyme-linked immunosorbent assay (Millipore, Cat. #EZRMI-13K) according to the manufacturer's instructions.

Homeostasis Model for Insulin Resistance Test (HOMA-IR):

HOMA-IR values were calculated from the fasting blood glucose (mgl/dL)×fasting plasma insulin (ng/ml) divided by 405.

mRNA and miRNA Quantification:

RNA was extracted using TRI reagent (Sigma-Aldrich, Israel) according to the manufacturer's protocol, followed by RNA concentration measurement (Nanodrop, Thermo, Wilmington, Del.) and gel electrophoresis. cDNA synthesis (Promega, Madison, Wis.) was performed and mRNA levels were determined by quantitative real-time reverse transcriptase (ABI prism 7900HT, SYBR green master mix, Applied Biosystems, CA, USA). Unless otherwise noted, all measurements were normalized to nDufc as a housekeeping gene. MicroRNA levels were determined using microRNA quantification system (Quanta Biosciences, MD, USA).

MicroRNA-Target Predicted Structure and Binding Energy:

miRNA-target binding energy and structure were predicted using the RNAhybrid algorithm.

Cholinesterase Activity:

levels of catalytic activity in mice tissues and sera were measured using the Ellman assay as described previously Hanin et al., Hum Mol Genet 23, 4569-4580 (2014).

Immunoblots:

Samples were lysed using a 0.01 M Tris HCl pH=7.4, 1 M NaCl, 1 mM EGTA, and 1% TX-100. SDS-PAGE separation and transfer to nitrocellulose followed standard procedures. Proteins were visualized using primary antibodies against SIRT1 (ab12193, Abcam, Mass., USA, 1:2000), Pten (sc-7974, Santa Cruz Biotechnology, TX, USA, 1:200), and GAPDH for normalization (2118, Cell Signaling, MA, USA, 1:2000), followed by horseradish peroxidase-conjugated goat anti rabbit antibodies (Jackson Laboratories, PA, USA, 1:10,000) and enhanced chemiluminescence (EZ-ECl, Biological Industries, Beit-Haemek, Israel).

Immunohistochemistry:

Paraffin slides were rehydrated by washing in xylene and serial dilutions of ethanol in water. Heat-induced antigen retrieval involved boiling slides in 10 mM pH 6 citrate buffer for 10 min. Hydrogen peroxide methanol quench was performed for slides later developed with 3,30-diaminobenzidine tetrahydrochloride (DAB). After washing, slides were incubated with 150 ml/slide of blocking buffer (4% normal serum, 0.05% TWEEN20 and 0.3% triton X-100) for 60 min, followed by over-night incubation at 4° C. with primary antibody diluted in the blocking buffer. Slides were then washed and incubated with biotin conjugated secondary antibody for 2 h, after which detection was performed by streptavidin-conjugated Cy (Jackson, West Grove, Pa.). Nuclear staining with 40,6-diamidino-2-phenylindole (DAPI) was used as counter-staining. Antibodies used include: anti FoxO3(SC-11351, Santa Cruz Biotechnology, TX, USA), P300 (SC-585, Santa Cruz Biotechnology, TX, USA), Arginase1 (SC-13851). Antibodies dilution: 1:200.

H&E Staining:

Small pieces of liver tissues were dissected from experimental animals and fixed in 4% paraformaldehyde, alcohol-dehydrated, paraffin-embedded, and sectioned to a mean thickness of 7 µm. Morphology was assessed using Hematoxylin and Eosin (H&E) stain.

Triglyceride Quantification:

Liver triglycerides were extracted from snap-frozen hepatic tissue stored at −80° C. Triglyceride measurement was performed using a Triglyceride Quantification Kit (ab65336, Abcam, Mass., USA). Samples were homogenized in 5% Nonidet P-40 dissolved in ddw, and heated twice to 80° C. in a water bath for 5 min and subsequently cooled to room temperature. After centrifugation to remove any insoluble material, samples were diluted 10-fold with distilled water. Assay procedure and detection has been performed according to manufacturer's instruction and quantitated using a fluorometric assay.

Free Fatty Acid Quantification:

Serum and liver free fatty acids were measured using a kit (ab65341, Abcam, Mass., USA). 5-10 µL serum from each mouse or 10 mg tissue which was then diluted 1:100 were used. Fluorometric assay was performed according to manufacturer's instructions.

Lipid Profile Measurement:

HDL and LDL/VLDL-cholesterol assay kit was used to measure serum VLDL/LDL and HDL-cholesterol concentrations (ab65390, Abcam, Mass., USA). 100 µL of serum from each mouse was mixed with 100 µL of precipitation buffer to separate out the HDL and LDL/VLDL. Assays were performed according to manufacturer's instructions and quantitated using a fluorometric assay.

Oil-Red O Staining:

To detect natural lipids in liver tissue, frozen samples were embedded in Tissue-Tek (1437365, Fisher Scientific, PA, USA), and 12 µm thick sections were cut, and dried for 10 minutes at room temperature. Slides were then stained with oil red O (ORO) (00625 Sigma Aldrich), incubated for 5 minutes with the ORO solution, washed with tap water for 30 minutes and mounted in ImmuMount (Thermo 9990402).

Aspartate Aminotransferase Activity Assay:

Aspartate Aminotransferase (AST) activity was determined using a kit (Sigma Aldrich MAK055). 50 mg liver tissue was homogenized in 200 µL ice-cold AST assay buffer, centrifuged at 13,000 g for 10 minutes to remove insoluble material. 5 µL of the supernatant were then added to 45 µL AST assay buffer. AST quantification was performed according to manufacturer's instructions.

Cell Lines:

Cells were grown in a humidified atmosphere at 37° C., 5% $CO_2$. C2C12 cells were grown in DMEM. Media was supplemented with 10% FBS, 2 mM L-glutamine, 1,000 units/ml penicillin, 0.1 mg/ml streptomycin sulfate, and 0.25 microgram/ml amphotericin B (Beit-Haemek, Israel). Transfection was performed using HiPerfect transfection reagent (Qiagen).

Fluidigm:

Expression of selected miRNA-132 targets and metabolic transcripts was determined using a high-throughput microfluidic qRT-PCR instrument (BioMark, Fluidigm, San Francisco, Calif.). Preamplified cDNA samples were mixed with TaqMan PreAmp Master Mix (Applied Biosystems) and DDW and pipetted into the Dynamic Fluidigm Array 96×96 chip. Amplification reaction product was cleaned using Exonuclease I (New England Biolabs, Ipswitch Mass.), and diluted 1:5 in Tris-EDTA buffer, pH=8. qRT-PCR mix was prepared using 2× SsoFast EvaGreen Supermix with low ROX (Biorad, Hercules Calif.). Priming and loading was performed using IFC Controller HX (BioMark). All qRT-PCR reactions were performed using the GE 96×96 PCR+ Melt v2.pcl protocol. Data analysis involved BioMark Real-Time PCR Analysis Software Version 2.0 (Fluidigm), and the ΔCt method was applied. Multiple housekeeping genes were used for normalization.

Statistics:

Statistical significance was calculated using Student's t-test or by one- or two-way ANOVA with LSD post-hoc, where appropriate. ±SEM is shown for all graphs.

Bioinformatic Analysis:

MiRNA-132 candidate targets were identified by using the following bioinformatic tools: miRanda, microCosm, PITA, miRWalk, DIANA microT CDS algorithms. The search allowed minimal 7-base pair seed region. The scores of each target in all the algorithms were then multiplied by the number of predicted binding sites between the miRNAs and the predicted target transcripts, and normalized to a value between 0 and 1. To incorporate the prediction values from each algorithm, the normalized value for each interaction was summed and all the predicted target transcripts were normalized again to a value between 0 and 1. To perform pathway enrichment analysis we then chose a threshold of 0.05 combined score, and the selected genes were then clustered using the DAVID functional annotation clustering tool. The gene list was normalized to the entire mouse genome, which served as a background. The top 4 developmental-relevant pathways were then chosen, and expanded for a gene list. To summarize the prediction of the target for each gene we scored 0 for no prediction and 1 for a prediction. For example, the insulin signaling pathway included 29 genes but only the fatty acid biosynthesis and glycolysis were included in the table. To further explore the phenotype of the gene, knockout or null mutations were searched for the gene name using the Mouse Genome Database).

Results

Peripherally Restricted miRNA-132 Excess Induces an NAFLD Phenotype

Figures 7A, 7B:
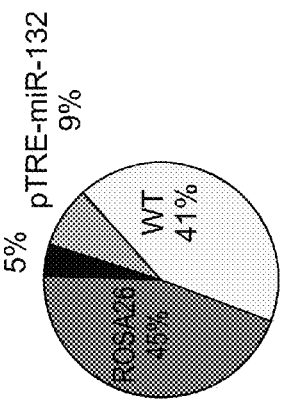
Figure 7C:
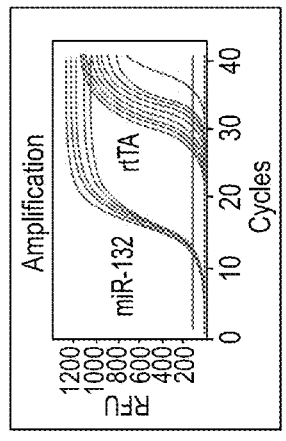
Figure 7D:
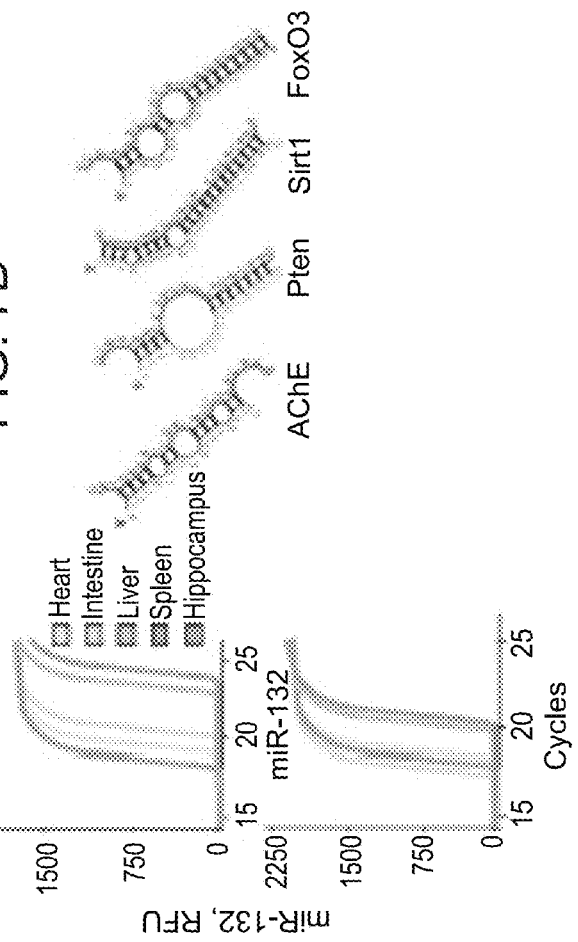
Figures 7E, 7F:
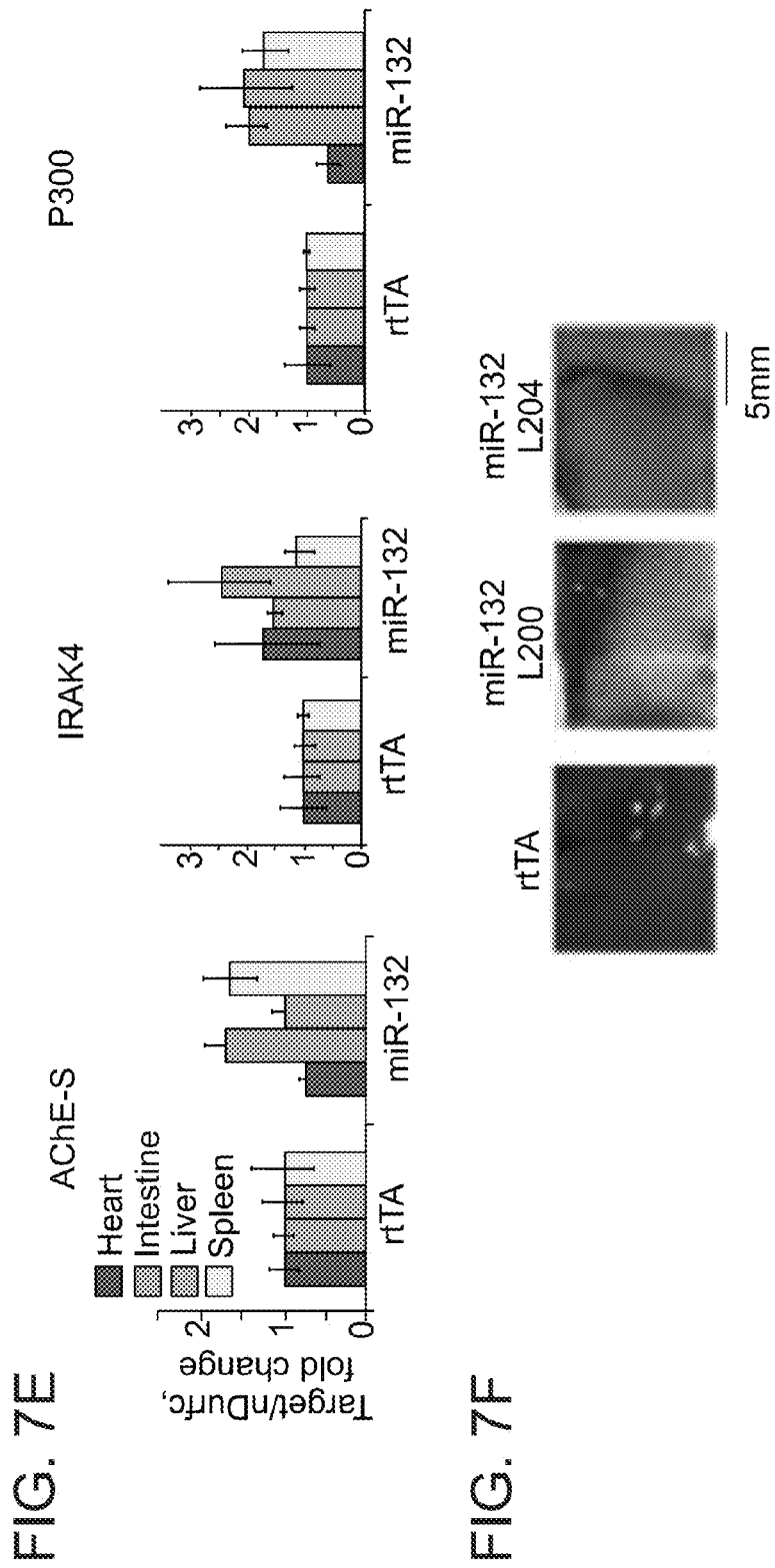

To induce peripherally restricted overexpression of miRNA-132, Tet-on founder mice were engineered to overexpress pre-miRNA-132 under control of the Gt(ROSA) 26Sor promoter and the ColA1 locus of the reverse tetracycline controlled trans-activator (rtTA) followed by a downstream β-globin poly-A. These mice were mated with another line with constitutive expression of a doxycycline-inducible rtTA protein that binds in trans to the $TRE_{mod}$ element; the progeny rtTA-miRNA-132 mice express miRNA-132 both in its endogenous host tissues and in ColA1-positive ones (FIG. 1B, FIG. 7A). Only 4.8% of the offspring mice were double transgenic, unlike the expected Mendelian 50% ratio (FIG. 7B), possibly due to leakiness of the Tet-on system, and the excess miRNA-132 effect on embryonic development. Mice from the highest miRNA-132 expressing line showed pronounced miRNA-132 overexpression in the heart, intestine, liver, spleen but not hippocampus (FIG. 1C and FIG. 7C). This expression pattern was, predictably accompanied by reduced hepatic levels of miRNA-132 targets compared to those in rtTA littermates (by 37%, 21%, and 24% for FoxO3, Pten and Sirt1, respectively FIG. 1D and FIG. 7D,E). This decline led to massive liver decreases in the Sirt1 and Pten proteins in miRNA-132 tg mice compared to rtTA littermates (FIG. 1E). This effect was extended to the level of biological function: hydrolytic AChE activity was down regulated in the serum, intestine and spleen, but not in the heart and hippocampus (FIG. 1F). It may be concluded that rtTA-miRNA-132 mice present a bona-fide model of peripherally restricted and functionally effective miRNA-132 excess.

A bioinformatics analysis was performed to search for predicted miRNA-132 targets using multiple prediction algorithms (miRanda, microcosm, PITA, miRWalk, DIANA microT-CDS). This was followed by pathway enrichment analysis that predicted multileveled involvement in embryogenesis. The top developmental-relevant processes included Insulin signaling, fatty acid biosynthesis, glycolysis, axon guidance, dorsal-ventral axis formation and TGFβ signaling (Table 1, herein below).

TABLE 1

Predicted miRNA-132 targets that are enriched in the top 4 KEGG pathways.
Insulin signaling pathway
Count: 29, P-Value: 0.002, Benjamini: 0.035

| Genes | Microcosm | PITA | miRWalk | MicroRNA.org | DIANA | Score | Phenotype |
|---|---|---|---|---|---|---|---|
| INSR | 0 | 1 | 0 | 0 | 0 | 0.126 | |
| PDPK1 | 0 | 1 | 0 | 1 | 0 | 0.124 | Embryogenesis defects, impaired forebrain development, die by mid gestation. |
| PIK3CA | 1 | 0 | 0 | 0 | 0 | 0.093 | Embryonic death associated with growth retardation. |
| Pik3r1 | 0 | 1 | 1 | 1 | 0 | 0.304 | Perinatal lethality associated with hepatic necrosis, chylous ascites and hypoglycemia. |
| Srebf1 | 0 | 1 | 0 | 1 | 0 | 0.132 | Die between day 11.5-14.5. Decreased circulating triglycerides |
| prkaa2 | 0 | 0 | 1 | 1 | 0 | 0.051 | — |
| PRKACB | 0 | 1 | 0 | 1 | 0 | 0.126 | — |
| Hk2 | 0 | 1 | 0 | 1 | 0 | 0.125 | Growth retardation, die around E8.5. |

To compare this model with the impact of brain-spanning miRNA-132 excess, mice were engineered with miRNA-132 expression under the constitutive H1 promoter, expressed in the brain as well. However, H1-miRNA-132 excess interrupted normal embryonic development: it was found 4/76 (5.2%) transgenic embryos and 1/32 (3.1%) resorbed embryo on day E10.5, but by day E14.5 and at P21, there were no transgene carriers out of 58 embryos and 19 resorbed ones, or 84 pups. Thus, global excess of miRNA-132 becomes incompatible with survival between days E10.5 and E14.5, possibly due to its suppression of notch signaling.

RtTA-miRNA-132 mice of two independent lines fed with regular chow diet (RCD) showed Doxycycline-potentiated and aging-related weight increases that were independent of the transgene's positional effect or gender and were also observed off-doxycycline, albeit in a considerably less pronounced manner (FIG. 2A). These two and an additional pTRE-miRNA-132 double transgenic line further presented extremely pale livers, and histological analysis identified microvesicular and macrovesicular liver steatosis (FIG. 2B-D, FIG. 7F. Liver triglycerides were increased (FIG. 2E), but the levels of serum and liver free fatty acids remained unchanged (FIG. 2F). LDL/VLDL cholesterol was increased, but HDL levels were sustained (FIG. 2G). Fluidic chamber RT-PCR analysis revealed significant elevation in several pro-steatotic transcripts in the pTRE-miRNA-132 mice, including SREBP1c, FAS and APOB. Inversely, numerous anti-steatotic transcripts were downregulated, including AOX, ABCA1, PGC1a, PEPCK, Cyp7a1 and PPARa. (FIG. 2H), suggesting that peripherally restricted excess of miRNA-132 initiates brain-independent hepatic steatosis and reduces lipolysis.

Antisense Oligonucleotide Suppression of miRNA-132 Reverses Liver Hyperlipidemia:

Having found that peripheral excess of transgenic miRNA-132 induced a fatty liver phenotype, the present inventors next asked if endogenous miRNA-132 excess is causally involved with liver steatosis and, if so, whether suppressing this excess would reverse the liver steatosis. To address these questions, diet-induced obese (DIO) C57bl/6J mice that were fed a high-fat diet regime for 11 weeks were used. These mice were injected with a 16-mer LNA-based oligonucleotide complementary to miR-132 (anti-miRNA-132, AM132; SEQ ID NO: 7) (FIG. 3A). DIO mice were heavier in weight compared to littermate controls fed with RCD (FIG. 3B). They also showed 6-fold elevated hepatic levels of miRNA-132 (FIG. 3C), similar to the hepatic miRNA-132 elevation in Cholestasis patients[34]. However, their NAFLD and biochemical parameters were rapidly and impressively receded following intravenous AM132 injection (3.3 mg/kg for three successive days). By 7 days post-treatment, DIO mice showed drastic reduction of liver miRNA-132 levels (FIG. 3D), suggesting efficient miRNA-132 knockdown in-vivo. Progressive decreases of liver size and weight brought treated mice to values of RCD-fed mice between 7-14 days post-treatment (representative picture and quantification in FIG. 3E, H, I). These results supported the working hypothesis and indicated causal involvement of miRNA-132 in the hyperlipidemia of fattened, non-transgenic mice as well.

Figure 8A:
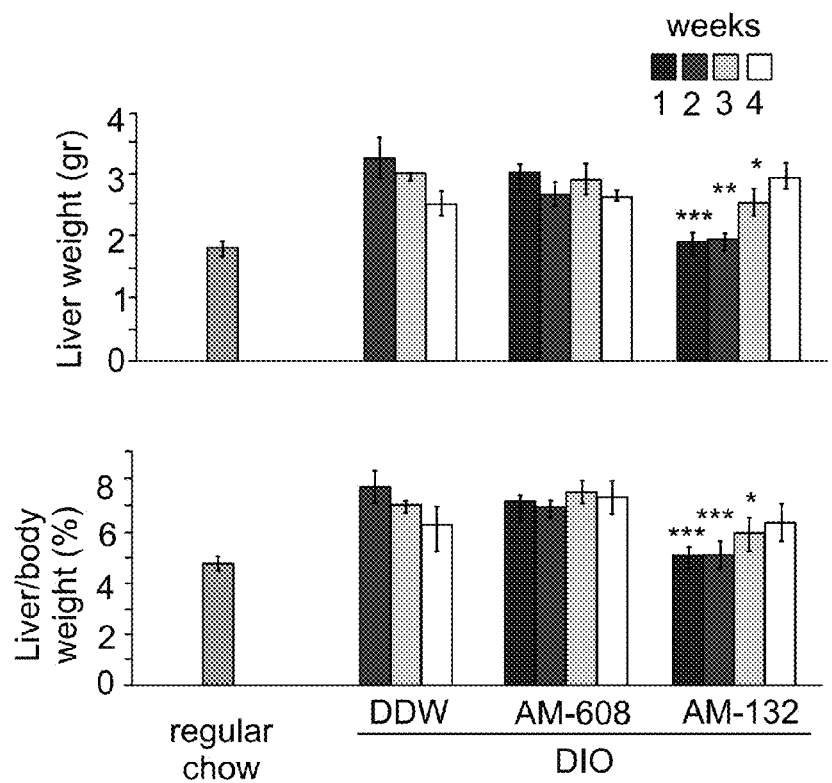
Figure 8B:
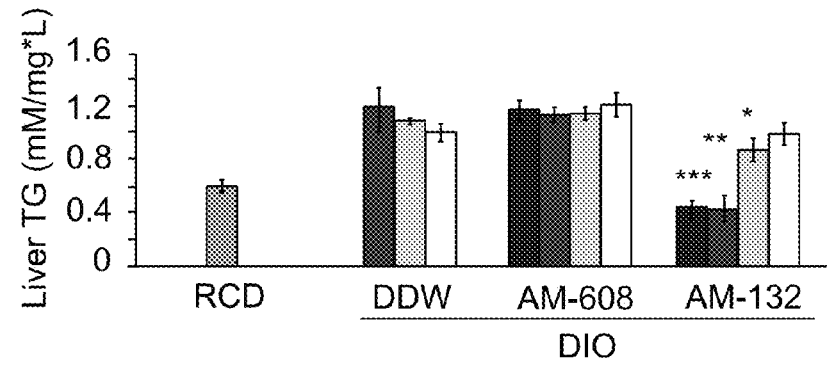
Figure 9A:
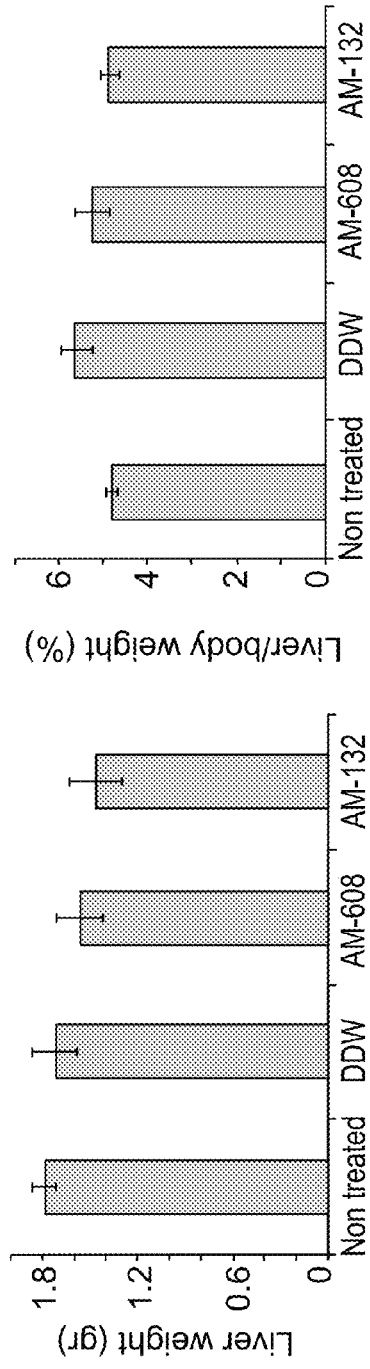
Figure 9B:
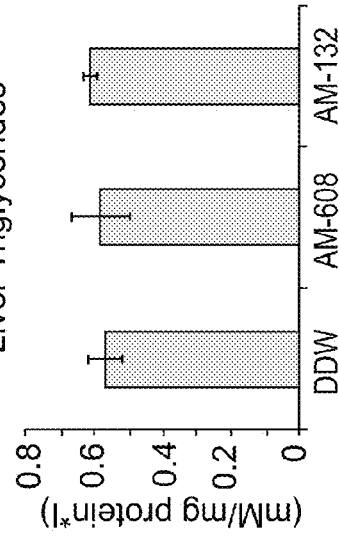
Figure 9C:
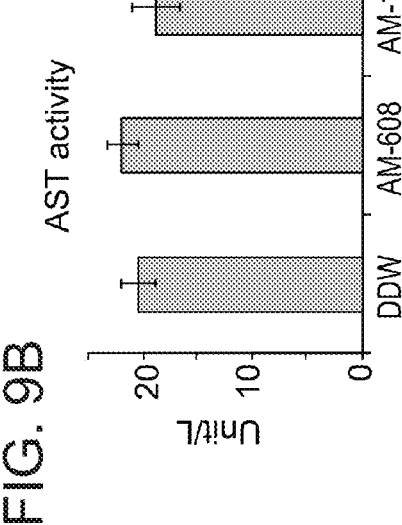
Figure 9D:
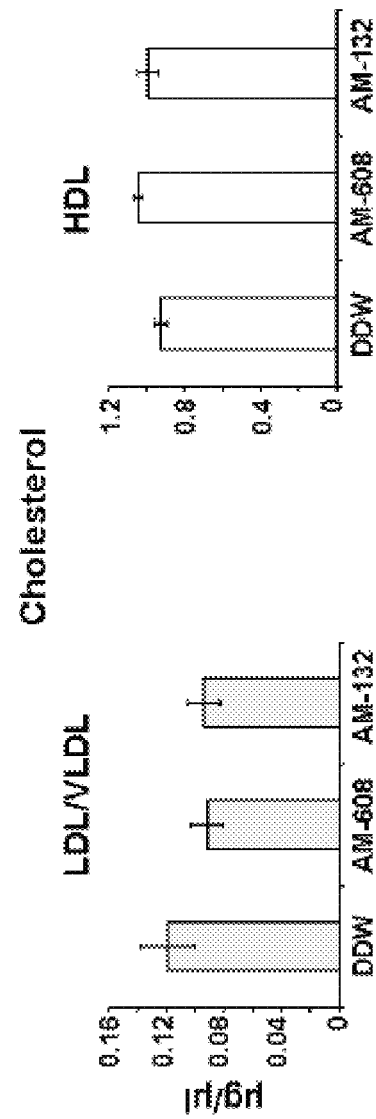

A control anti-miRNA-608 (AM608) AntagomiR for the primate-specific miRNA-608 that is absent in mice[35], and shows no predicted metabolic-related mouse target transcripts, showed similar liver and liver weight, liver triglycerides, LDL/VLDL and HDL values to those of DDW treated mice (FIG. 8A-C), excluding a non-specific oligonucleotide effect. In contrast, general histology and Oil-red-o staining of liver sections from AM132-treated mice, which kept consuming high fat diet, showed gradual fat vacuole clearance, represented by smaller vacuoles at day 5 and their complete absence at days 7-14 post-treatment (FIG. 3F-I). Treatment further induced decreases in liver triglycerides, with similar kinetics to that of liver weight; reaching levels of RCD-fed mice at days 7-14 (FIG. 3K). LDL/VLDL levels likewise declined to those of RCD-fed mice (FIG. 3L), while HDL remained unchanged. Also, untreated RCD-fed mice and DIO mice treated with AM132 or control LNA all showed similar Aspartate amino transferase (AST) activity, excluding overt liver toxicity in the LNA-treated mice (FIG. 8D). In comparison, lean RCD-fed mice treated with AM132 showed unchanged normal liver and liver weights, AST activity, liver triglycerides, LDL/VLDL and HDL (FIGS. 9A-D), suggesting specificity of the AM132 treatment for NAFLD liver. It may be concluded that AM132 selectively reduces liver steatosis in DIO mice.

High fat diet induces metabolic syndrome (MetS) in DIO mice, and the miRNA-132 target FoxO3 is inactivated by insulin via a phosphatidylinositol-3-kinase/AKT-dependent pathway. To investigate if miRNA-132 contributes to this aspect of the MetS phenotype as well, the impact of AM132 treatment on insulin regulation of glucose homeostasis was measured. By 7 days post AM132 treatment, DIO mice presented declined levels of fasting serum insulin compared to controls (1.55±0.17 vs. 2.43±0.16 ng/ml, FIG. 3M). Also, their homeostatic model assessment (HOMA) index was reduced compared to controls (0.45±0.05 vs. 0.74±0.05, FIG. 3N), and intravenous glucose tolerance test (GTT) showed faster decline of blood glucose (FIG. 3O); together suggesting improved insulin sensitivity. Nevertheless, by 10 days post-treatment, AM132-treated mice showed similar intravenous insulin tolerance test (ITT) values and similar fasting glucose levels to those of control mice (FIG. 8E). Overall these results suggest that at its peak effective time, AM132 slightly improved glucose tolerance by reducing insulin resistance.

Figure 4A:
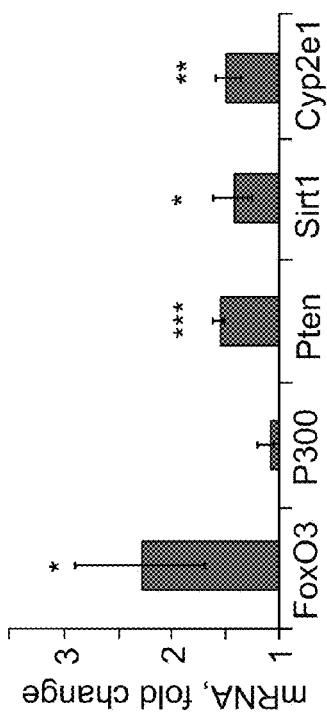
Figure 4B:
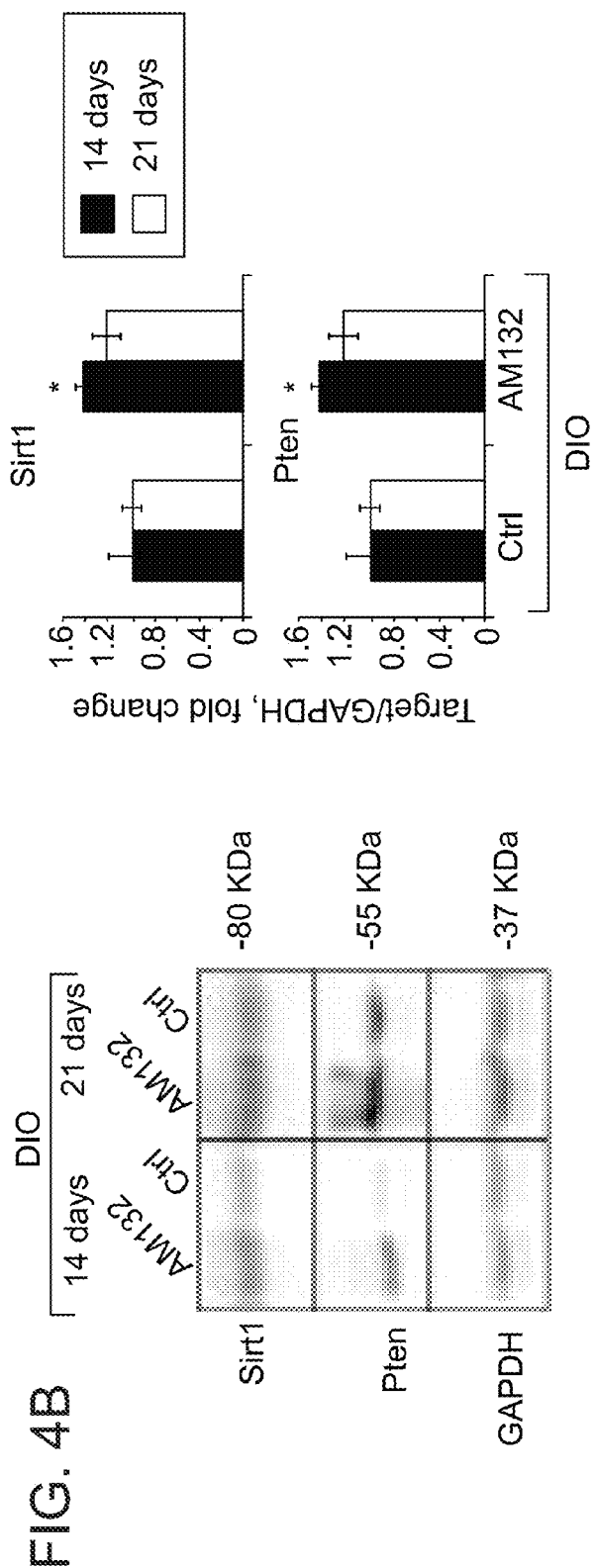
Figure 4C:
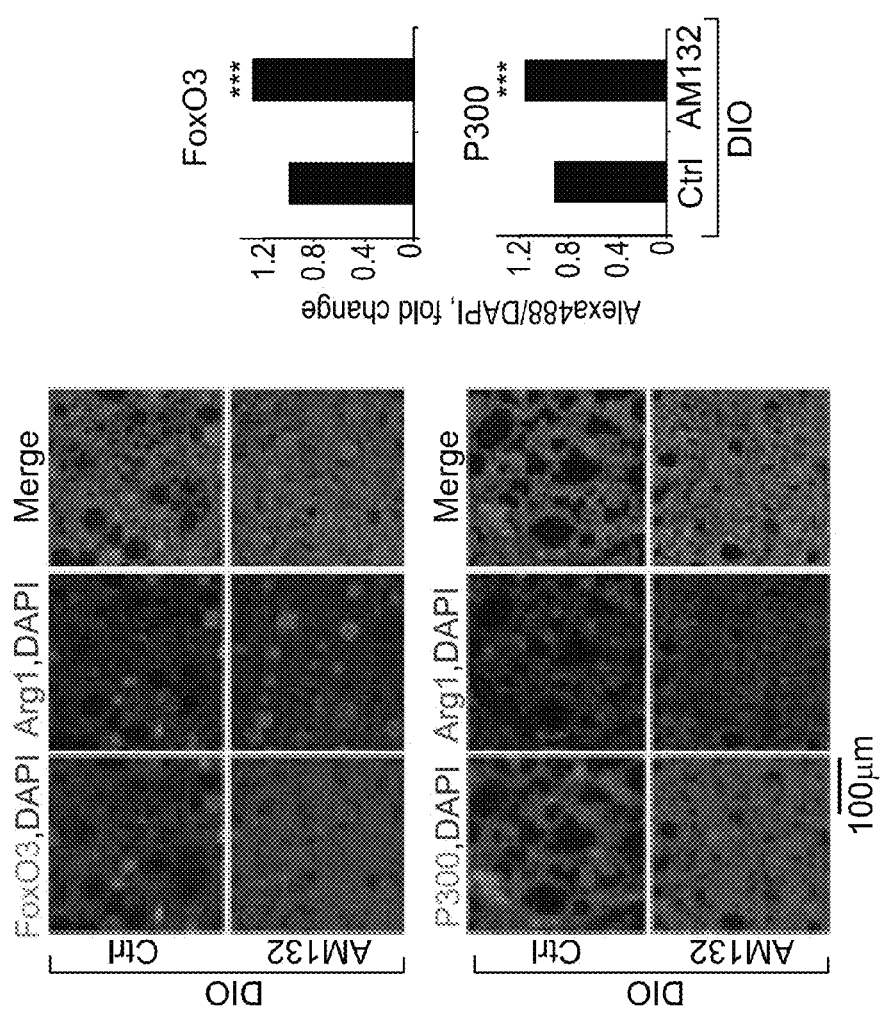

AM132 Elevates miRNA-132 Targets in a Sequence and Dose-Dependent Manner:

To address the molecular mechanism of action through which AM132 reduces the NAFLD hallmarks, the hepatic levels of miRNA-132 target transcripts were quantified using fluidic chamber qRT-PCR tests (Fluidigm). FoxO3, Pten, Sirt1 and Cyp2e1 were all up-regulated (FIG. 4A). By 7-14 days post-treatment, the levels of the FoxO3, Pten, Sirt1 and P300 proteins were also elevated (FIG. 4B, C). Moreover, the anti-steatotic ABCA1, AOX, PEPCK, PGC1a, Ehhadh, L-PK and FXR transcripts were elevated 7 days post-AM132 treatment, whereas the pro-steatotic GPAT and SREBP2 transcripts were reduced (FIG. 4D). In some cases, AM132 treatment completely reversed the changes in transcript levels observed in the transgenic pTRE-miRNA-132 mice, demonstrating generally enhanced lipolysis and some reduction in lipogenesis. The global reversal of NAFLD hallmarks under this peripherally restricted AM132 treatment established the causal involvement of hepatic miRNA-132 in the NAFLD phenotype.

Figure 10B:
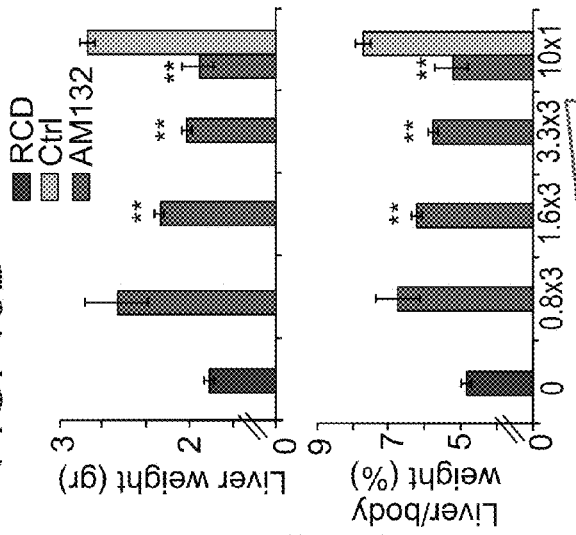
Figure 10D:
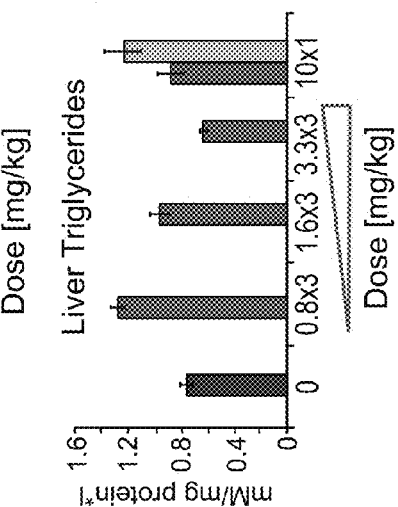
Figure 10A:
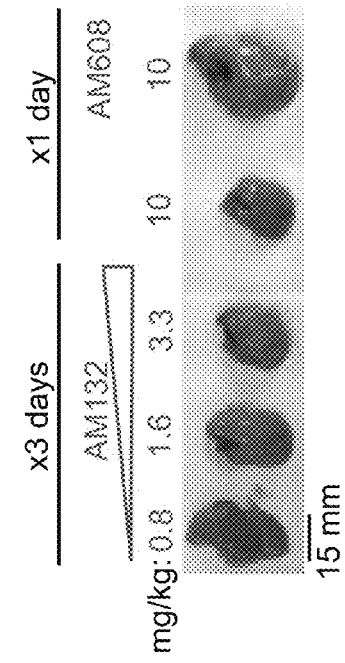
Figure 10C:
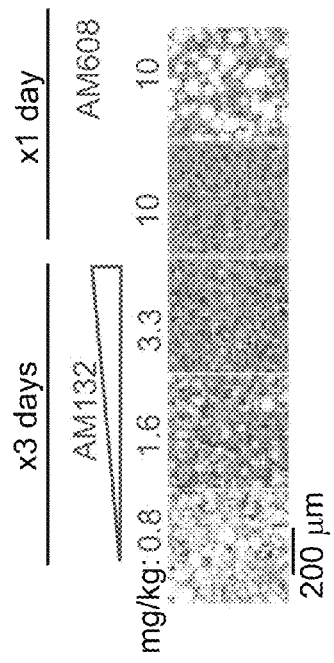
Figure 10E:
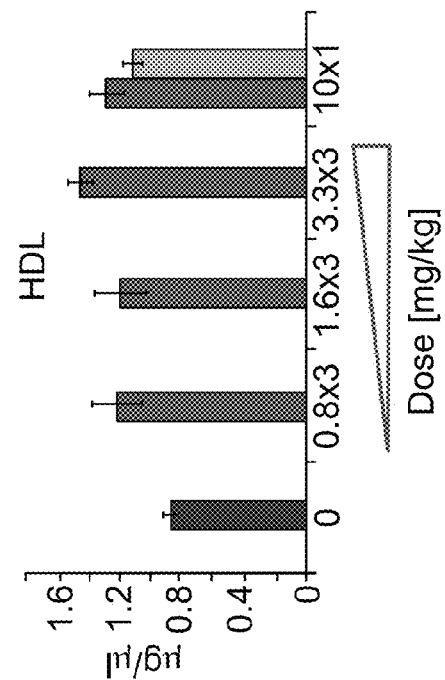
Figure 10F:
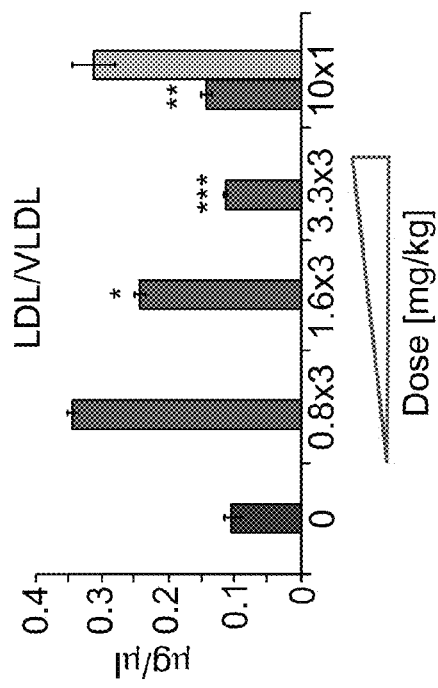

To explore the therapeutic window and chemical composition of AM132, mice were intravenously injected with either escalating doses of 0.8, 1.6 and 3.3 mg/Kg AM132 for 3 successive days or by a single 10 mg/Kg dose. By 7 days post-treatment, mice presented dose-dependent reductions of liver and liver/body weights, with the single day 10 mg/Kg treatment being as efficient as 3-day 3.3 mg/Kg regime (FIGS. 10A, B). Dose dependence was likewise observed for fat vacuole clearance (FIG. 10C), liver triglycerides (FIG. 10D), and LDL/VLDL but not HDL (FIGS. 10 E, F). A similar therapeutic effect was also achieved for a 2-O-methyl and fully phosphorothioated backbone AM132 oligonucleotide, which induced similar liver weight, liver/body weight and LDL/VLDL reductions to those of the LNA compound (FIGS. 11A,B). Thus, AM132 operated in a sequence and dose-dependent manner regardless of its specific chemical structure.

In another experiment, C57Bl/6 mice were fed with high fat diet for 11 weeks, and injected intravenously with AM132 or control (10 mg/kg for a single day). 2 weeks later, these mice were injected again with the same oligonucleotide and dose. 11 days after the second injection, mice were sacrificed. Liver weight and liver/body weight of AM132-treated mice were significantly reduced, similar to mice singly injected with of AM-132 (FIGS. 13A-B).

Figure 5A:
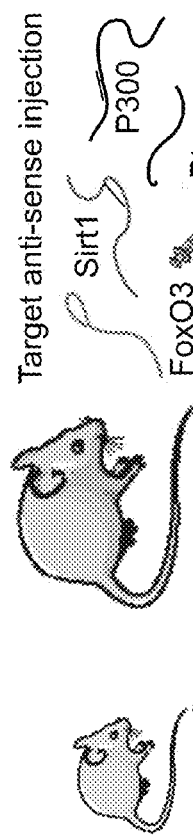
Figure 5B:
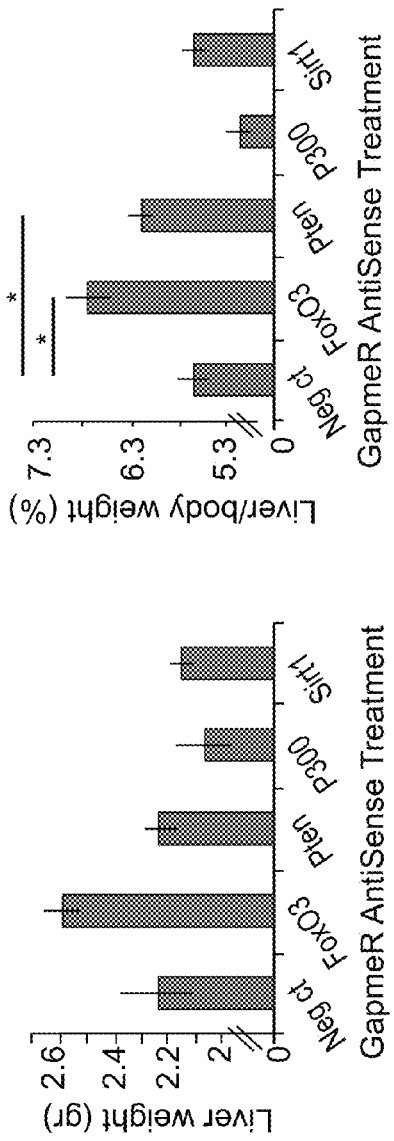
Figure 5C:
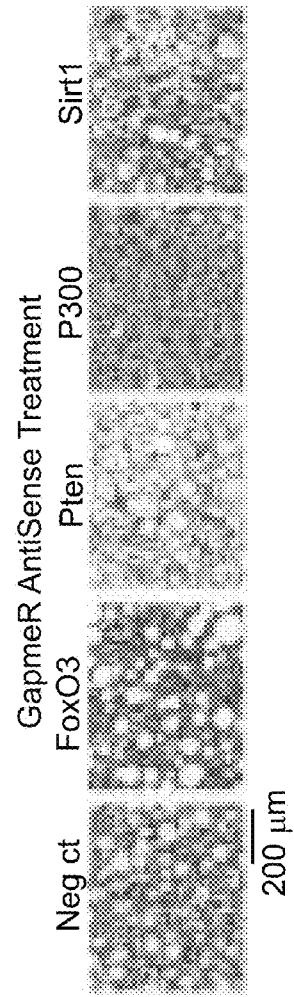
Figures 5D, 5E:
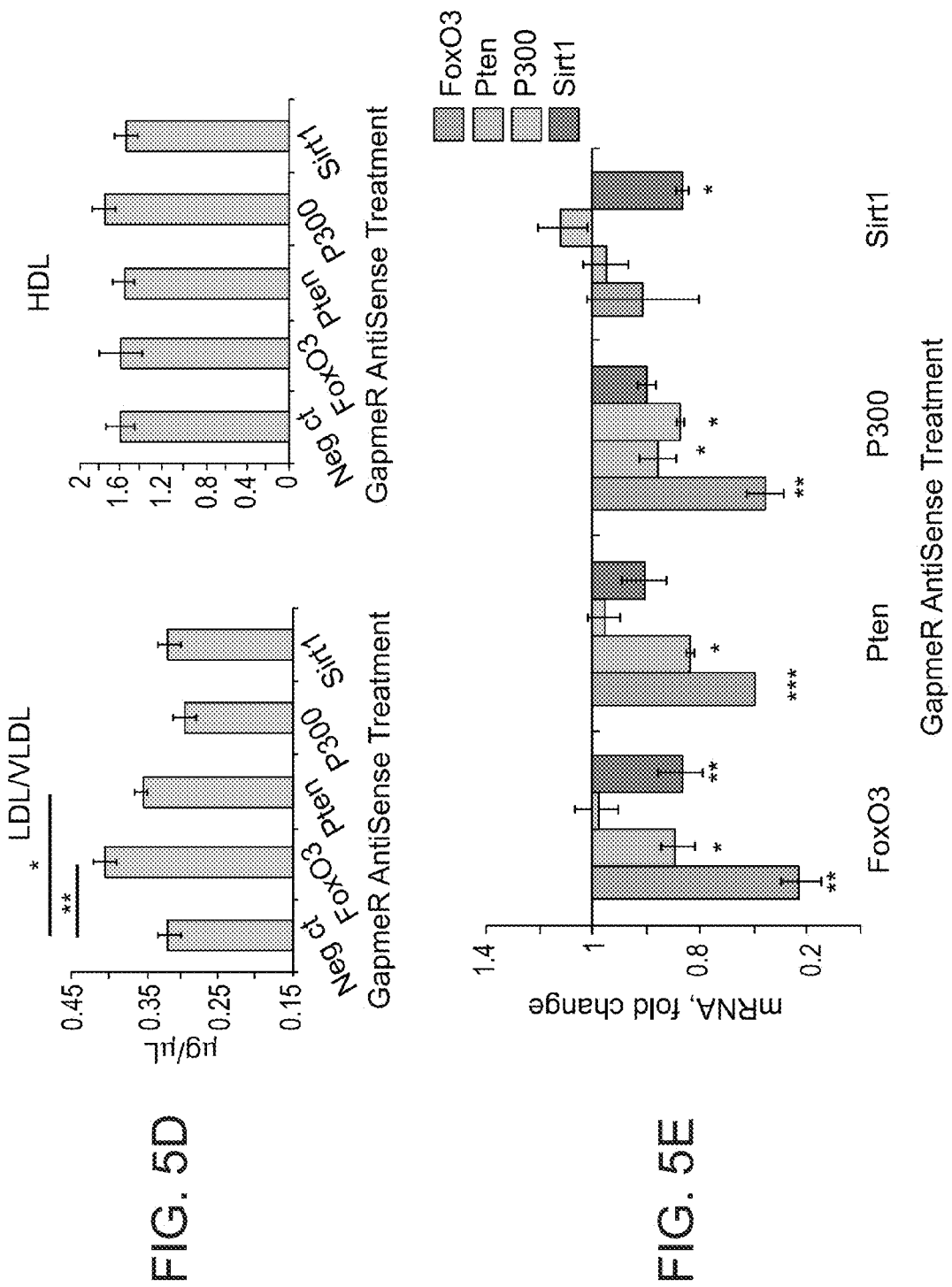
Figure 12A:
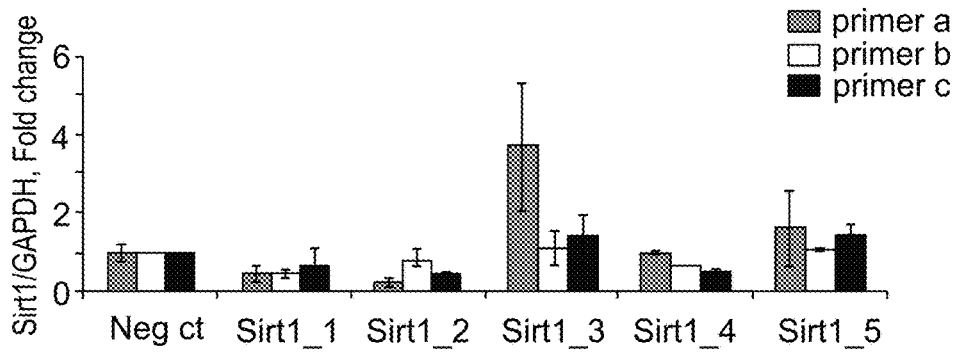
Figure 12B:
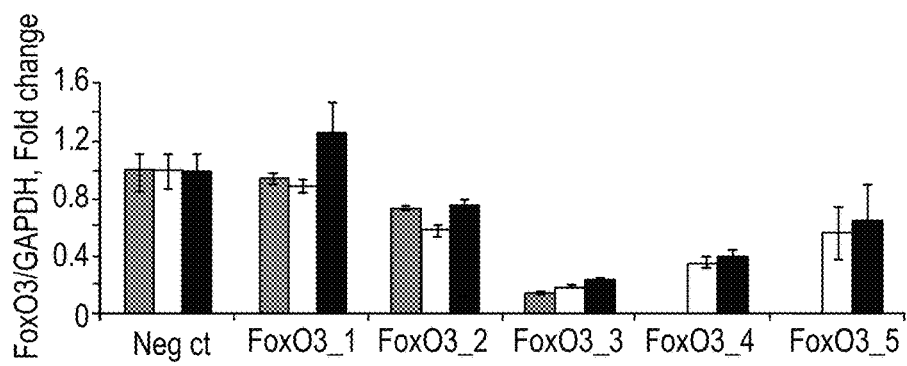
Figure 12C:
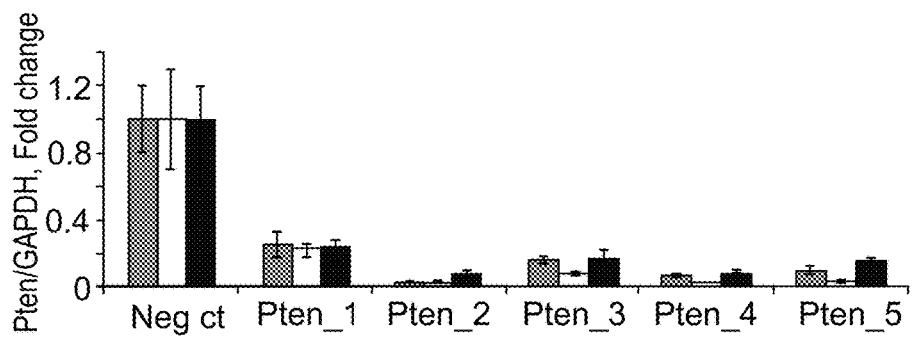
Figures 12D, 12E:
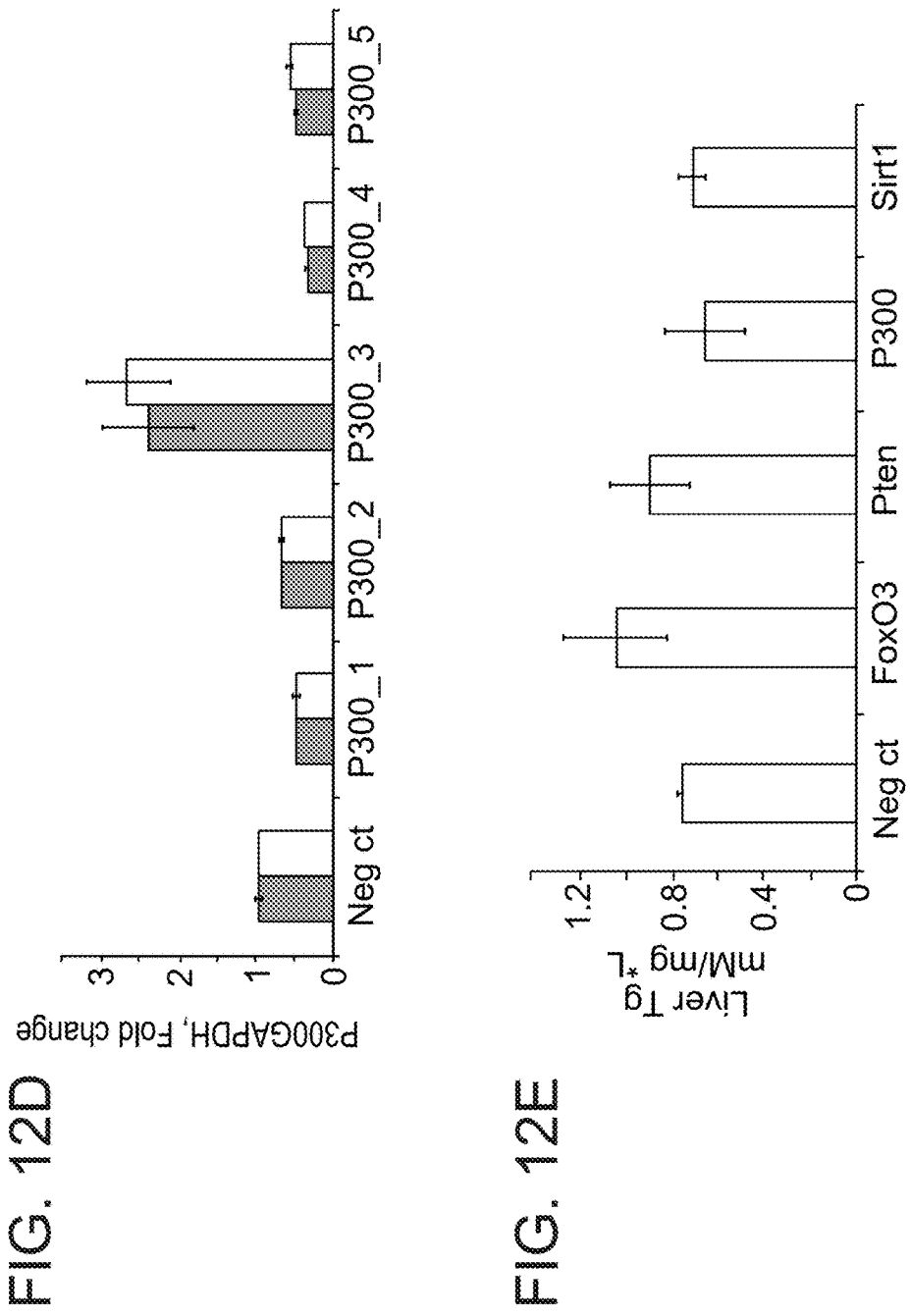

Direct Knockdown of FoxO3 and Pten Mimics the Hepatic Impact of miRNA-132 in DIO Mice:

Peripheral excess of miRNA-132 could potentially induce its hepatic consequences through one or several of those miRNA-132 targets whose levels were increased in the engineered and fattened mice. To explore the relative contribution of each of these targets to the development of steatosis, DIO mice following 9 weeks of high fat diet were exposed to a single intravenous injection of 10 mg/kg LNA-protected antisense (AS) GapmeRs for either FoxO3, Pten, P300 or Sirt1, all selected from several candidate GapmeRs compared to a negative control GapmeR by in-vitro validation of knockdown efficacy in C2C12 cells (FIG. 5A and FIGS. 12A-D). This in vivo treatment as well was peripherally restricted and liver-targeted, since injected oligonucleotides tend to accumulate in the liver[33] and fail to penetrate through the blood-brain-barrier[40]. By 7 days post-treatment, knockdown of FoxO3 and Pten in DIO mice significantly increased liver/body weight, whereas P300 knockdown reduced it and Sirt1 knockdown mice showed no difference (FIG. 5B). Mice treated with FoxO3-AS, Pten-AS, P300-AS and Sirt1-AS revealed macrovesicular and microvesicular steatosis, reduced vacuole counts or no visible change, respectively in Hematoxylin/Eosin staining of liver sections (FIG. 5C). FoxO3-AS and Pten-AS treatment further increased LDL/VLDL levels in treated mice; HDL levels remained unchanged in all groups (FIG. 5D). Liver triglycerides showed a similar trend (FIG. 12E). Importantly, knockdown of FoxO3, which reduced its levels by 78% also resulted in reduced Pten and Sirt1 levels; also, 37% knockdown of Pten affected FoxO3 by 60%, lower levels than Pten-AS itself, and 33% knockdown of P300 also reduced FoxO3 and Pten, however with limited steatosis. Sirt1 knockdown by 34% did not affect other targets (FIG. 5E). These findings support the notion of key roles for FoxO3 and Pten in liver steatosis, whereas P300 acts inversely to limit this pathology.

AM132 Selectively Reduces LDL/VLDL Levels in LDLR-/- Mice with Familial-Like Hyperlipidemia:

Familial hypercholesterolemia (FH) involves impaired lipid homeostasis due to one of >1400 different mutations in the LDL receptor (LDLR) gene. FH patients are often lean with no significant difference in their BMI, yet accumulate fat in various tissues. To determine whether AM132 treatment may be valuable for this disease as well, RCD-fed LDLR-/- mice with inherited hypercholesterolemia and high LDL/VLDL levels were exposed to 3.3 mg/kg AM132 treatment for 3 successive days (FIG. 6A). By 7 days post-treatment, treated LDLR-/- mice showed 90% less miRNA-132 in the liver (FIG. 6B), normal liver and liver/body weight (FIG. 6C), and decreased liver LDL/VLDL but not HDL levels (FIG. 6D). Liver triglycerides showed a trend toward reduction (FIG. 6E), and miRNA-132 targets (FIG. 6F) and several metabolic transcripts were elevated (FIG. 6E); suggesting treatment-enhanced lipolysis, which in turn leads to reduced LDL/VLDL production[38,39]. Taken together, these findings indicate that AM132-mediated enhancement of hepatic anti-steatotic transcripts might be beneficial also to patients with familial hyperlipidemia.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating a fatty liver disease in a subject in need thereof, comprising administering to the subject a therapeutically effective amount of a polynucleotide, which is substantially complementary to a nucleotide sequence of human miR-132, wherein said polynucleotide is at least 12-30 nucleotides in length, thereby treating the fatty liver disease, wherein said fatty liver disease is selected from the group consisting of hypertriglyceridemia, steatohepatitis and hypercholesterolemia.

2. A method of treating obesity in a subject in need thereof, comprising administering to the subject a therapeutically effective amount of a polynucleotide, which is substantially complementary to a nucleotide sequence of human miR-132, wherein said polynucleotide is at least 12-30 nucleotides in length, thereby treating the obesity in the subject.

3. An article of manufacture comprising a polynucleotide, which is substantially complementary to a nucleotide sequence of human miR-132 and an-anti lipid agent.

4. The method of claim 1, wherein said polynucleotide downregulates an amount of said human miR-132.

5. The method of claim 1, wherein said polynucleotide downregulates an activity of said human miR-132.

6. The method of claim 1, wherein said polynucleotide comprises the nucleic acid sequence as set forth in SEQ ID NO: 8 or at least 15 consecutive bases thereof.

7. The method of claim 6, wherein said polynucleotide comprises the nucleic acid sequence as set forth in SEQ ID NO: 7 or SEQ ID NO: 10.

8. The method of claim 1, wherein said polynucleotide comprises a modified internucleotide linkage selected from the group consisting of phosphoroamidate, phosphorothiate, phosphorodithioate, boranophosphate, alkylphosphonate and methylinemethylimino.

9. The method of claim 1, wherein said polynucleotide comprises a modified nucleic acid unit selected from the group consisting of locked nucleic acid unit, 2'-O-alkyl ribonucleic acid unit, 2'amine ribonucleic acid unit, peptide nucleic acid unit, 2'fluoro-ribo nucleic acid unit, morpholino nucleic acid unit, cyclohexane nucleic acid unit and a tricyclonucleic acid unit.

10. The method of claim 1, wherein said nucleic acid unit comprises a modified nucleic acid unit selected from the group consisting of locked nucleic acid unit, 2'-O-methyl ribonucleic acid unit, and 2'O-methoxy-ethyl ribonucleic acid unit.

11. The method of claim 1, wherein said polynucleotide comprises a locked nucleic acid, a 2'-O-methyl ribonucleic acid, or a mixed nucleic acid-locked nucleic acid.

12. The method of claim 1, wherein each of the nucleotides of said polynucleotide is a locked nucleic acid.

13. The method of claim 1, wherein said administering is effected once per day.

14. The method of claim 1, wherein said administering is effected once a week.

15. The method of claim 1, wherein a dose of said polynucleotide is between 1 µg/kg body weight-100 mg/kg body weight per administration.

16. The method of claim 1, wherein the subject does not have an eye disease.

17. The method of claim 1, wherein the subject does not have a neurodegenerative disease.

18. The method of claim 1, wherein the subject does not have cancer.

19. The method of claim 1, wherein said hypercholesterolemia is a familial hypercholesterolemia.

* * * * *

SEQUENCE LISTING

```
<160> NUMBER OF SEQ ID NOS: 11

<210> SEQ ID NO 1
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 1
ggaatcgcgg gcccagtgtc                                                  20

<210> SEQ ID NO 2
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 2
gggcggagaa tgggcggaac                                                  20

<210> SEQ ID NO 3
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 3
tactgtggga accggaggta                                                  20

<210> SEQ ID NO 4
<211> LENGTH: 24
<212> TYPE: DNA
<213> ORGANISM: Artificial Sequence
<220> FEATURE:
<223> OTHER INFORMATION: Single strand DNA oligonucleotide

<400> SEQUENCE: 4
tgaaatttgt gatgctattg cttt                                             24

<210> SEQ ID NO 5
<211> LENGTH: 21
<212> TYPE: DNA
<213> ORGANISM: Artificial Sequence
<220> FEATURE:
<223> OTHER INFORMATION: Single strand DNA oligonucleotide

<400> SEQUENCE: 5
acagtctaca gccatggtcg c                                                21

<210> SEQ ID NO 6
<211> LENGTH: 21
<212> TYPE: DNA
<213> ORGANISM: Artificial Sequence
<220> FEATURE:
```

<223> OTHER INFORMATION: Single strand DNA oligonucleotide

<400> SEQUENCE: 6
cgctctgtat ctgcccaaac c                                              21

<210> SEQ ID NO 7
<211> LENGTH: 16
<212> TYPE: DNA
<213> ORGANISM: Artificial Sequence
<220> FEATURE:
<223> OTHER INFORMATION: oligonucleotide antagomir

<400> SEQUENCE: 7
atggctgtag actgtt                                                    16

<210> SEQ ID NO 8
<211> LENGTH: 22
<212> TYPE: DNA
<213> ORGANISM: Artificial Sequence
<220> FEATURE:
<223> OTHER INFORMATION: oligonucleotide antagomir

<400> SEQUENCE: 8
cgaccatggc tgtagactgt ta                                             22

<210> SEQ ID NO 9
<211> LENGTH: 22
<212> TYPE: RNA
<213> ORGANISM: Artificial Sequence
<220> FEATURE:
<223> OTHER INFORMATION: oligonucleotide antagomir

<400> SEQUENCE: 9
uaacagucua cagccauggu cg                                             22

<210> SEQ ID NO 10
<211> LENGTH: 15
<212> TYPE: DNA
<213> ORGANISM: Artificial Sequence
<220> FEATURE:
<223> OTHER INFORMATION: oligonucleotide antagomir

<400> SEQUENCE: 10
cgaccatggc tgtag                                                     15

<210> SEQ ID NO 11
<211> LENGTH: 15
<212> TYPE: DNA
<213> ORGANISM: Artificial Sequence
<220> FEATURE:
<223> OTHER INFORMATION: oligonucleotide antagomir
<220> FEATURE:
<221> NAME/KEY: misc_feature
<222> LOCATION: (1)..(2)
<223> OTHER INFORMATION: locked nucleic acids (LNA) (2'-O-methyl)
<220> FEATURE:
<221> NAME/KEY: misc_feature
<222> LOCATION: (4)..(4)
<223> OTHER INFORMATION: locked nucleic acids (LNA) (2'-O-methyl)
<220> FEATURE:
<221> NAME/KEY: misc_feature
<222> LOCATION: (6)..(6)
<223> OTHER INFORMATION: locked nucleic acids (LNA) (2'-O-methyl)
<220> FEATURE:
<221> NAME/KEY: misc_feature
<222> LOCATION: (9)..(10)
<223> OTHER INFORMATION: locked nucleic acids (LNA) (2'-O-methyl)
<220> FEATURE:
<221> NAME/KEY: misc_feature

```
<222> LOCATION: (13)..(13)
<223> OTHER INFORMATION: locked nucleic acids (LNA) (2'-O-methyl)
<220> FEATURE:
<221> NAME/KEY: misc_feature
<222> LOCATION: (15)..(15)
<223> OTHER INFORMATION: locked nucleic acids (LNA) (2'-O-methyl)

<400> SEQUENCE: 11
cgaccatggc tgtag                                                    15
```